US008524669B2

(12) United States Patent
Kufe et al.

(10) Patent No.: US 8,524,669 B2
(45) Date of Patent: Sep. 3, 2013

(54) MUC-1 CYTOPLASMIC DOMAIN PEPTIDES AS INHIBITORS OF CANCER

(75) Inventors: Donald W. Kufe, Wellesley, MA (US); Surender Kharbanda, Natick, MA (US)

(73) Assignees: Dana-Farber Cancer Institute, Inc., Boston, MA (US); Genus Oncology, LLC, Vernon Hills, IL (US)

( * ) Notice: Subject to any disclaimer, the term of this patent is extended or adjusted under 35 U.S.C. 154(b) by 403 days.

(21) Appl. No.: 12/580,865

(22) Filed: Oct. 16, 2009

(65) Prior Publication Data

US 2010/0125055 A1 May 20, 2010

Related U.S. Application Data

(60) Provisional application No. 61/106,380, filed on Oct. 17, 2008, provisional application No. 61/177,109, filed on May 11, 2009.

(51) Int. Cl.
*A61P 35/00* (2006.01)

(52) U.S. Cl.
USPC .......................................... 514/19.3; 514/6.5

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. | 424/450 |
| 5,912,232 A | 6/1999 | Talmadge | |
| 6,548,643 B1 | 4/2003 | McKenzie et al. | 530/395 |
| 7,118,862 B2 | 10/2006 | Kufe et al. | 435/7.23 |
| 7,247,297 B2 | 7/2007 | Weichselbaum et al. | 424/93.2 |
| 7,556,935 B2 | 7/2009 | Kufe et al. | 435/15 |
| 2002/0044943 A1 | 4/2002 | Longenecker et al. | |
| 2005/0042209 A1 | 2/2005 | Kufe et al. | 514/44 |
| 2005/0053606 A1 | 3/2005 | Kufe et al. | 424/155.1 |
| 2005/0089957 A1 | 4/2005 | Goddard et al. | |
| 2005/0271650 A1* | 12/2005 | Freimark et al. | 424/130.1 |
| 2005/0282744 A1 | 12/2005 | Hollingsworth et al. | 530/300 |
| 2006/0293234 A1 | 12/2006 | Schroeder | 514/2 |
| 2007/0071675 A1 | 3/2007 | Wu et al. | 424/1.49 |
| 2007/0105767 A1 | 5/2007 | Kharbanda et al. | 514/8 |
| 2007/0202134 A1 | 8/2007 | Kufe et al. | 536/24.5 |
| 2007/0207209 A1* | 9/2007 | Murphy et al. | 424/484 |
| 2008/0286264 A1 | 11/2008 | Kufe | 435/7.23 |
| 2009/0047307 A1* | 2/2009 | Harrop et al. | 424/232.1 |
| 2009/0087437 A1 | 4/2009 | Kufe | 435/4 |
| 2009/0092600 A1 | 4/2009 | Kufe | 435/7.1 |
| 2009/0098054 A1 | 4/2009 | Kufe | 435/7.1 |
| 2009/0136520 A1 | 5/2009 | Kufe | 435/7.23 |
| 2009/0232812 A1 | 9/2009 | Kufe et al. | 424/155.1 |
| 2010/0125055 A1 | 5/2010 | Kufe et al. | 514/21.4 |
| 2011/0251246 A1 | 10/2011 | Kufe et al. | |

FOREIGN PATENT DOCUMENTS

| | | |
|---|---|---|
| EP | 1538164 | 6/2005 |
| WO | WO 00/34468 | 6/2000 |
| WO | WO 01/18035 | 3/2001 |
| WO | WO 01/57068 | 8/2001 |
| WO | WO2005/101021 | 10/2005 |
| WO | WO 2008/121767 | 10/2008 |

OTHER PUBLICATIONS

Cancer Drug Design and Discovery. Neidle, Stephen, ed., Elsevier/ACademic Press, 2008, p. 427-431.*
Gura, T. Systems for Identifying New Drugs Are Often Faulty, Science, 1997, 278, pp. 1041-1042.*
Auerbach. R. et al, Angiogenesis assays: Problems and pitfalls, Cancer and Metastasis Reviews, 2000, 19, pp. 167-172.*
Jain R. K., Barriers to Drug Delivery in Solid Tumors, Scientific American, 1994, pp. 58-65.*
Sporn, B and Suh, N, Chemoprevention of cancer, Carcinogenesis, 2000, 21, pp. 525-530.*
Spicer et al, Molecular Cloning and Analysis of the Mouse Homologue of the Tumor-associated Mucin, MUC1R, eveals Conservation of Potential O-Glycosylation Sites, Transmembrane, and Cytoplasmic Domains and a Loss of Minisatellite-like Polymorphism, The Journal of Biological Chemistry, 1991, 266, pp. 15099-15109.*
Ahmad et al.,"MUC1 oncoprotein activates the IkappaB kinase beta complex and constitutive NF-kappaB signalling," *Nat. Cell Biol.*, 9:1419-1427, 2007.
Ahmad et al., "Triterpenoid CDDO-Me blocks the NF-kappaB pathway by direct inhibition of IKKbeta on Cys-179," *J. Biol. Chem.*, 281:35764-9, 2006.
Anderson et al., "Multiple myeloma: New insights and therapeutic approaches," *Hematology*, 1:147-165, 2000.
Arkin et al., "Structural aspects of oligomerization taking place between the transmembrane a-helices of bitopic membrane proteins," *Biochimica et Biophysica Acta*, 1565:347-363, 2002.
Beatty et al., "Cutting edge: Transgenic expression of human MUC1 in IL-10 -/- Mice accelerates inflammatory bowel disease and progression to colon cancer," *J. Immunol..*, 179:735-739, 2007.
Begum et al., "Muc1 based breast cancer vaccines: role of post translational modifications," *J. Ayub. Med. Coll. Abbottabad.*, 20(4):130-133, 2008.
Kawano et al.,"MUC1 oncoprotein promotes growth and survival of human multiple myeloma cells," *International Journal of Oncology*, 33:153-159, 2008.
Kinlough et al., "Recycling of MUC1 is dependent on its palmitoylation," *The Journal of Biological Chemistry*, 281(17):121 12-12122, 2006.
PCT International Search Report and Written Opinion, issued in International patent Application No. PCT/US10/36436, dated Oct. 19, 2010.
Peczuh et al., "Peptide and protein recognition by designed molecules," *Chem. Rev.*, 100:2479-2494, 2000.
Raina et al., "Dependence on the MUC1-C oncoprotein in non-small cell lung cancer cells," Mol. Cancer Ther., 10(5):806-816, May 2011. E-published Mar. 18, 2011. Doi:10.1 158/1535-7163.mct-10-1050.
Yin et al., "MUC1-C oncoprotein suppresses reactive oxygen species-induced terminal differentiation of acute myelogenous leukemia cells," Blood., 1 17(18):4863-4870, May 5, 2011. E-published Mar. 21, 2011. D01:10.1182/blood-2010-296632.

(Continued)

*Primary Examiner* — Julie Ha
*Assistant Examiner* — Li Ni Komatsu
(74) *Attorney, Agent, or Firm* — Parker Highlander PLLC

(57) ABSTRACT

The invention provides for peptides from the Mucin 1 (MUC1) cytoplasmic domain and methods of use therefor. These peptides can inhibit MUC1 oligomerization, thereby preventing tumor cell growth, inducing tumor cell apoptosis and necrosis of tumor tissue in vivo.

26 Claims, 32 Drawing Sheets

(56) References Cited

OTHER PUBLICATIONS

Zhou et al., "MUC1 oncoprotein is a target for small molecule inhibitors," *Molecular Pharmacology*, Published online before print Feb. 23, 2011, Doi: 10.1124/mol.110.070797.

Hu et al.,"MUC1 cytoplasmic tail: a potential therapeutic target for ovarian cancer," *Future Drugs*, 6(8):1261-1271, 2006.

Kufe, "Human MUC1 oncoprotein is of functional importance fo the development of prostate cancer," Award Number: W81XWH-08-0093, Annual Report, prepared for U.S. Army Medical Research and Materiel Command, Mar. 2009.

Li and Cozzi, "MUC1 is a promising therapeutic target for prostate cancer therapy," *Current Cancer Drugs Targets*, 7:259-271, 2007.

PCT International Search Report and Written Opinion, issued in International application No. PCT?US2009/061051, dated Nov. 26, 2010.

Tsutsumida et al., "RNA interference suppression of MUC1 reduced the growth rate and metastatic phenotype of human pancreatic cancer cells," *Clin. Cancer Res.*, 12(10):2976-2987, 2006.

Abe and Kufe, "Structural analysis of the DF3 human breast carcinoma-associated protein," *Cancer Res.*, 49(11):2834-2839, 1989.

Ahmad et al.,"MUC1-C oncoprotein functions as a direct activator of the nuclear factor-κβ p65 transcription factor," *Cancer Research*, 69: 7013, 2009.

Baldus et al., "MUC1 and nuclear beta-catenin are coexpressed at the invasion front of colorectal carcinomas and are both correlated with tumor prognosis," *Clin. Cancer Res.*, 10(8):2790-2796, 2004.

Bitler et al., "Intracellular MUC1 peptides inhibit cancer progression," *Clin. Canc. Res.*, 15 (1): 100-109, 2009.

Fischer, "Cellular uptake mechanisms and potential therapeutic utility of peptidic cell delivery vectors: Progress 2001-2006," *Medicinal Research Reviews*, 27 (6): 755-795, 2007.

Hodel et al., "The three-dimensional structure of the autoproteolytic, nuclear pore-targeting domain of the human nucleoporin Nup98," *Mol. Cell*, 10(2):347-58, 2002.

Huang et al., "MUC1 cytoplasmic domain coactivates Wnt target gene transcription and confers transformation," *Cancer Biol. Ther.*, 2 (6): 702-706, 2003.

Huang et al., "MUC1 oncoprotein blocks glycogen synthase kinase 3beta-mediated phosphorylation and degradation of beta-catenin," *Cancer Res.*, 65:10413-10422, 2005.

Joshi et al., "MUC1 oncoprotein is a druggable target in human prostate cancer cells," *Mol. Cancer Ther.*, 8 (11): 3056-3065, 2009.

Kau et al., "Nuclear transport and cancer: from mechanism to intervention," *Nat. Rev. Cancer*, 4(2):106-17, 2004.

Khodarev et al., "Cooperativity of the MUC1 oncoprotein and STAT1 pathway in poor prognosis human breast cancer," *Oncogene*, 2009.

Kufe et al., "Differential reactivity of a novel monoclonal antibody (DF3) with human malignant versus benign breast tumors," *Hybridoma*, 3 (3):223-232, 1984.

Kufe, "Functional targeting of the MUC1 oncogene in human cancers," *Cancer Biology & Therapy*, 8 (13): 1201-1207, 2009.

Kufe, "Mucins in cancer: function, prognosis and therapy," *Nat. Rev. Cancer*, 9 (12): 874-885, 2009.

Kufe, "Targeting the human MUC1 oncoprotein: a tale of two proteins," *Cancer Biol. Ther.*, 7 (1): 81-84, 2008.

Leng et al., "Nuclear import of the MUC1-C oncoprotein is mediated by nucleoporin Nup62," *The Journal of Biological Chemistry*, 282 (27): 19321-19330, 2007.

Levitin et al., "The MUC1 SEA module is a self-cleaving domain," *J. Biol. Chem.*, 280:33374-33386, 2005.

Li et al., "DF3/MUC1 Signaling in Multiple Myeloma Cells is Regulated by Interleukin-7," *Cancer Biol. Ther.*, 2:187-193, 2003b.

Li et al., "Heregulin targets gamma-catenin to the nucleolus by a mechanism dependent on the DF3/MUC1 oncoprotein," *Mol. Cancer Res.*, 1 (10):765-775, 2003c.

Li et al., "Human DF3/MUC1 carcinoma-associated protein functions as an oncogene," *Oncogene*, 22 (38): 6107-6110, 2003.

Li et al., "Interaction of glycogen synthase kinase 3beta with the DF3/MUC1 carcinoma-associated antigen and beta-catenin," *Mol. Cell Biol.*, 18:7216-7224, 1998.

Li et al., "The c-Src tyrosine kinase regulates signaling of the human DF3/MUC1 carcinoma-associated antigen with GSK3 beta and beta-catenin," *J. Biol. Chem.*, 276(9):6061-6064, 2001.

Li et al., "The epidermal growth factor receptor regulates interaction of the human DF3/MUC1 carcinoma antigen with c-Src and beta-catenin," *J. Biol. Chem.*, 276:35239-35242, 2001.

Ligtenberg et al., "Cell-associated episialin is a complex containing two proteins derived from a common precursor," *J. Biol. Chem.*, 267 (9), 6171-6177, 1992.

Macao, "Autoproteolysis coupled to protein folding in the SEA domain of the membrane-bound MUC1 mucin," *Nat. Struct. Mol. Biol.*, 13 (1), 71-76, 2006.

Raina et al., "Direct targeting of the mucin 1 oncoprotein blocks survival and tumorigenicity of human breast carcinoma cells," *Cancer Res.*, 69 (12): 5133-5141, 2009.

Raina et al., "MUC1 oncoprotein blocks nuclear targeting of c-Abl in the apoptotic response to DNA damage," *EMBO J.*, 25:3774-3783, 2006.

Raina et al., "The MUC1 oncoprotein activates the anti-apoptotic phosphoinositide 3-kinase/Akt and Bcl-xL pathways in rat 3Y1 fibroblasts," *J. Biol. Chem.*, 279 (20):20607-20612, 2004.

Ramasamy et al., "The MUC1 and galectin-3 oncoproteins function in a microRNA-dependent regulatory loop," *Mol. Cell*, 27 (6):992-1004, 2007.

Ren et al., "Human MUC1 carcinoma-associated protein confers resistance to genotoxic anticancer agents," *Cancer Cell*, 5 (2):163-175, 2004.

Ren et al., "MUC1 oncoprotein functions in activation of fibroblast growth factor receptor signaling," *Mol. Cancer Res.*, 4 (11): 873-883, 2006.

Ren et al., "MUC1 oncoprotein is targeted to mitochondria by heregulin-induced activation of c-Src and the molecular chaperone HSP90," *Oncogene*, 25 (1):20-31, 2006.

Ren et al., "Protein kinase C delta regulates function of the DF3/MUC1 carcinoma antigen in beta-catenin signaling," *J. Biol. Chem.*, 277 (20):17616-17622, 2002.

Schroeder et al., "MUC1 overexpression results in mammary gland tumorigenesis and prolonged alveolar differentiation," *Oncogene*, 23 (34):5739-5747, 2004.

Schroeder et al., "Transgenic MUC1 interacts with epidermal growth factor receptor and correlates with mitogen-activated protein kinase activation in the mouse mammary gland," *J. Biol. Chem.*, 276(16):13057-13064 2001.

Truscott et al., "A J-protein is an essential subunit of the presequence translocase-associated protein import motor of mitochondria," *J. Cell Biol.*, 163(4):707-713, 2003.

Vermeer et al., "Segregation of receptor and ligand regulates activation of epithelial growth factor receptor," *Nature*, 422(6929):322-6, 2003.

Wei et al., "Human MUC1 oncoprotein regulates p53-responsive gene transcription in the genotoxic stress response," *Cancer Cell*, 7 (2):167-178, 2005.

Wei et al.,"MUC1 oncoprotein stabilizes and activates estrogen receptor alpha," *Mol. Cell.*, 21 (2): 295-305, 2006.

Weis, "Regulating access to the genome: nucleocytoplasmic transport throughout the cell cycle," *Cell*, 112(4):441-51, 2003.

Wen et al., "Nuclear association of the cytoplasmic tail of MUC1 and beta-catenin," *J. Biol. Chem.*, 278 (39):38029-38039, 2003.

Yamamoto et al., "Interaction of the DF3/MUC1 breast carcinoma-associated antigen and betacatenin in cell adhesion," *J. Biol. Chem.*, 272 (19):12492-12494, 1997.

Yin et al., "Human MUC1 carcinoma antigen regulates intracellular oxidant levels and the apoptotic response to oxidative stress," *J. Biol. Chem.*, 278 (37):35458-35464, 2003b.

Yin et al., "MUC1 oncoprotein activates the FOXO3a transcription factor in a survival response to oxidative stress," *J. Biol. Chem.*, 279 (44):45721-45727, 2004.

Yin et al., "MUC1 oncoprotein promotes autophagy in a survival response to glucose deprivation," *Int. J. Oncol.*, 34 (6): 1691-1699, 2009.

Yin et al., "Mucin 1 oncoprotein blocks hypoxia-inducible factor 1 alpha activation in a survival response to hypoxia," *J. Biol. Chem.*, 282 (1):257-266, 2007.

Young et al., "Molecular chaperones Hsp90 and Hsp70 deliver preproteins to the mitochondrial import receptor Tom70," *Cell.* 112 (1): 41-50, 2003.

Office Action issued in European Patent Application No. 09740811.6, dated Jun. 22, 2012.

English Translation of Office Communication issued in corresponding Chinese Patent Application 200980149998.9, dated Mar. 4, 2013.

English Translation of Ling et al."MUC1 C-terminal Heterodimer and Its Tumorgenicity," *Progress in Biochemistry and Biophysics*, 34(4): 375-381, 2007.

Ling et al."MUC1 C-terminal Heterodimer and Its Tumorgenicity," *Progress in Biochemistry and Biophysics*, 34(4): 375-381, 2007.

Notice of Allowance issued in U.S. Appl. No. 12/789,127, dated Jan. 23, 2012.

Office Communication issued in U.S. Appl. No. 12/789,127, dated Mar. 28, 2012.

Office Communication issued in U.S. Appl. No. 12/789,127, dated Jul. 5, 2012.

Response to Office Communication issued in U.S. Appl. No. 12/789,127, dated Apr. 30, 2012.

Response to Office Communication issued in U.S. Appl. No. 12/789,127, dated Jan. 4, 2013.

Supplementary European Search Report issued in European Patent Application No. 10781227.3, dated Dec. 3, 2012.

\* cited by examiner

B.

C.

MUC1-CD

CQCRRKNYGQLDIFPARDTYHPMSEYPTYHTHGRYVPPSSTDRSPYEKVSAGNGGSSLYTNPAVAAASL
(SEQ ID NO:62)

|  |  |  | SEQ ID NOS: |
|---|---|---|---|
| Endogenous | A I V Y L I A L A V C Q C R R K N Y G |  | 55 |
| GO-200-1B | Ac-A I V Y L-S5-A L A-S5-C Q C-R-R K N Y G-NH2 |  | 56 |
| GO-200-2B | Ac-A KK Y L-S5-A L A-B5-C Q C-S5-R K N Y –NH2 |  | 57 |
| GO-201 | NH2-[dR]9- C Q C R R K N Y G Q L D I F P –COOH | TFA | 3 |
| GO-202 | NH2-[dR]9- C Q C R R K N –COOH | TFA | 53 |
| GO-203 | NH2-[dR]9- dC dQ dC dR dR dK dN-COOH | TFA | 53 |
| GO-203-1 | Acetyl- [dR]9 - dC dQ dC dR dR dK dN –NH2 | TFA | 53 |
| GO-203-2 | Acetyl- [dR]9 - dC dQ dC dR dR dK dN –NH2 | HCL | 53 |
| GO-203a | NH2-dR- dR- dR - dC dQ dC dR dR dK dN dR -COOH | TFA | 58 |
| GO-203b | NH2-dR- dR- dC dQ dC dR dR dK dN dR -COOH | TFA | 58 |
| GO-203c | Acetyl-dR- dR - dC dQ dC dR dR dK dN- NH2 | TFA | 53 |
| GO-203-cyc | Acetyl- [dR]9 - dC dQ dC dR dR dK dN –NH2 | TFA | 53 |
| GO-203-cyc-1 | Acetyl-dR- dR - dC dQ dC dR dR dK dN- NH2 | TFA | 53 |
| GO-204 | NH2- dC dQ dC dR dR dK dN-[dR]9 -COOH | TFA | 53 |
| GO-205 | Acetyl- [dR]9 - dN dK dR dR dC dQ dC –NH2 | TFA | 59 |
| GO-206 | NH2- dN dK dR dR dC dQ dC--[dR]9 -COOH | TFA | 59 |
| GO-207 | NH2-[dR]9- dC dQ dC dR dR dK -COOH | TFA | 4 |
| GO-208 | NH2-[dR]9- dC dQ dC dR dR -COOH | TFA | 50 |
| GO-209 | NH2-[dR]9- dC dQ dC dR -COOH | TFA | 54 |
| GO-210 | NH2-[dR]9- dC dQ dC-COOH | TFA |  |
| CP-1 | NH2-[dR]9- A Q A R R K N Y G Q L D I F P -COOH | TFA | 60 |
| CP-2 | NH2-[dR]9- dA dQ dA dR dR dK dN-COOH | TFA | 61 |

FIG. 8

Figure 13 Effect of different MUC1-CD CQC-region peptides on the growth of triple negative breast carcinoma cells.

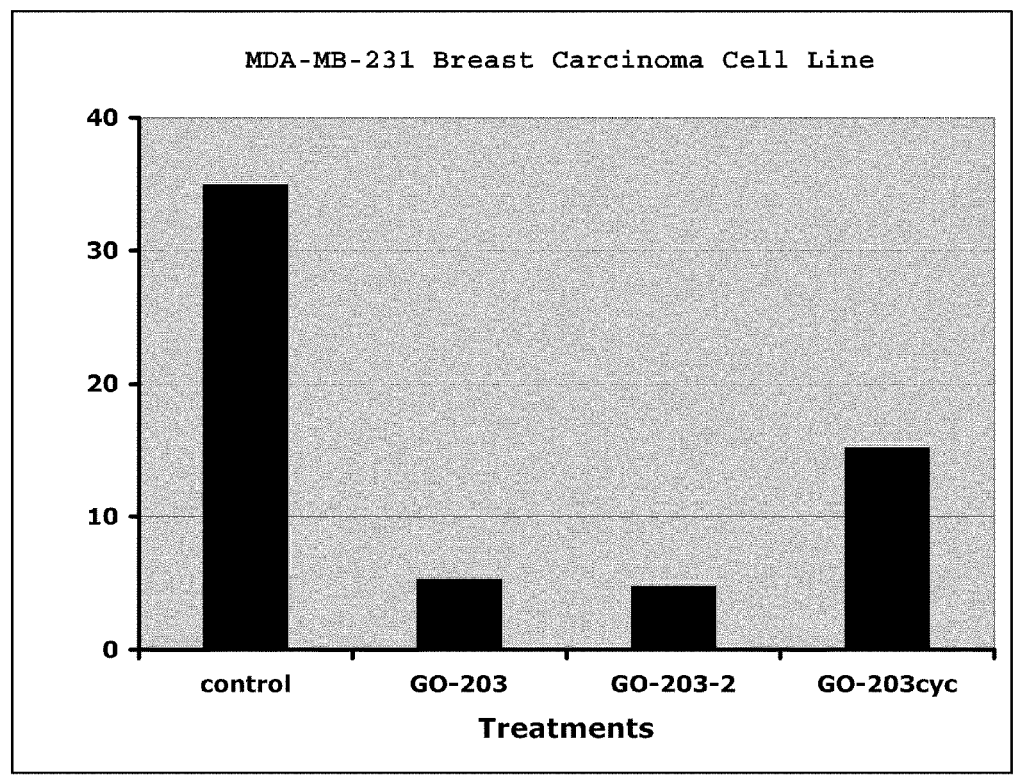

MDA-MB-231 triple negative breast carcinoma cells were treated with 5 µM of different MUC1-CD CQC-region peptides for 6 days. Viable cell number on day 6 was determined by trypan blue exclusion. The results demonstrate that treatment of MDA-MB-231 cells with different peptides was associated with significant inhibition of growth.

FIG. 15A-D

SEQUENCE LISTING

```
<160> NUMBER OF SEQ ID NOS: 62

<210> SEQ ID NO 1
<211> LENGTH: 72
<212> TYPE: PRT
<213> ORGANISM: Artificial
<220> FEATURE:
<223> OTHER INFORMATION: Synthetic peptide

<400> SEQUENCE: 1

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60
```

```
Val Ala Thr Ser Ala Asn Leu
 65                  70
```

```
<210> SEQ ID NO 2
<211> LENGTH: 159
<212> TYPE: PRT
<213> ORGANISM: Artificial
<220> FEATURE:
<223> OTHER INFORMATION: Synthetic peptide

<400> SEQUENCE: 2

Gly Ser Val Val Val Gln Leu Thr Leu Ala Phe Arg Glu Gly Thr Ile
 1               5                  10                  15

Asn Val His Asp Val Glu Thr Gln Phe Asn Gln Tyr Lys Thr Glu Ala
                20                  25                  30

Ala Ser Arg Tyr Asn Leu Thr Ile Ser Asp Val Ser Val Ser Asp Val
             35                  40                  45

Pro Phe Pro Phe Ser Ala Gln Ser Gly Ala Gly Val Pro Gly Trp Gly
         50                  55                  60

Ile Ala Leu Leu Val Leu Val Cys Val Leu Val Ala Leu Ala Ile Val
 65                  70                  75                  80

Tyr Leu Ile Ala Leu Ala Val Cys Gln Cys Arg Arg Lys Asn Tyr Gly
                 85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155
```

```
<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Cys Gln Cys Arg Arg Lys Asn Tyr Gly Gln Leu Asp Ile Phe Pro
 1               5                  10                  15
```

```
<210> SEQ ID NO 4
<211> LENGTH: 6
<212> TYPE: PRT
<213> ORGANISM: Artificial
<220> FEATURE:
<223> OTHER INFORMATION: Synthetic peptide

<400> SEQUENCE: 4

Cys Gln Cys Arg Arg Lys
 1               5
```

```
<210> SEQ ID NO 5
<211> LENGTH: 34
<212> TYPE: PRT
<213> ORGANISM: Artificial
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
```

```
                1               5                   10                  15
Glu Arg Pro Arg Ala Pro Ala Arg Ser Ala Ser Arg Pro Arg Arg Pro
                20                  25                  30
Val Glu

<210> SEQ ID NO 6
<211> LENGTH: 16
<212> TYPE: PRT
<213> ORGANISM: Artificial
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15
Gly Arg

<210> SEQ ID NO 10
<211> LENGTH: 11
<212> TYPE: PRT
<213> ORGANISM: Artificial
<220> FEATURE:
<223> OTHER INFORMATION: Synthetic peptide

<400> SEQUENCE: 10

Tyr Gly Arg Lys Lys Arg Arg Gln Arg Arg Arg
1               5                   10

<210> SEQ ID NO 11
<211> LENGTH: 9
<212> TYPE: PRT
<213> ORGANISM: Artificial
<220> FEATURE:
```

<223> OTHER INFORMATION: Synthetic peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

```
<210> SEQ ID NO 17
<211> LENGTH: 16
<212> TYPE: PRT
<213> ORGANISM: Artificial
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala
```

<210> SEQ ID NO 23
<211> LENGTH: 14
<212> TYPE: PRT
<213> ORGANISM: Artificial
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28

```
<211> LENGTH: 26
<212> TYPE: PRT
<213> ORGANISM: Artificial
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial
<220> FEATURE:
<223> OTHER INFORMATION: Synthetic peptide

<400> SEQUENCE: 32

Pro Pro Pro Pro Pro Pro Pro Pro Pro Pro Pro Pro
1               5                   10
```

```
<210> SEQ ID NO 33
<211> LENGTH: 18
<212> TYPE: PRT
<213> ORGANISM: Artificial
<220> FEATURE:
<223> OTHER INFORMATION: Synthetic peptide

<400> SEQUENCE: 33

Val Arg Leu Pro Pro Val Arg Leu Pro Pro Val Arg Leu Pro
1               5                   10                  15

Pro Pro

<210> SEQ ID NO 34
<211> LENGTH: 10
<212> TYPE: PRT
<213> ORGANISM: Artificial
<220> FEATURE:
<223> OTHER INFORMATION: Synthetic peptide

<400> SEQUENCE: 34

Pro Arg Pro Leu Pro Pro Arg Pro Gly
1               5                   10

<210> SEQ ID NO 35
<211> LENGTH: 30
<212> TYPE: PRT
<213> ORGANISM: Artificial
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial
<220> FEATURE:
<223> OTHER INFORMATION: Synthetic peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial
```

-continued

```
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 39
<211> LENGTH: 28
<212> TYPE: PRT
<213> ORGANISM: Artificial
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
```

```
<212> TYPE: PRT
<213> ORGANISM: Artificial
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu
```

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 6
<212> TYPE: PRT
<213> ORGANISM: Artificial
<220> FEATURE:
<223> OTHER INFORMATION: Synthetic peptide

<400> SEQUENCE: 49

Lys Arg Arg Cys Gln Cys
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Cys Gln Cys Arg Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Cys Gln Cys Arg Arg Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Cys Gln Cys Arg Arg Arg Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Cys Gln Cys Arg Arg Lys Asn
1               5

```
<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Cys Gln Cys Arg
1

<210> SEQ ID NO 55
<211> LENGTH: 19
<212> TYPE: PRT
<213> ORGANISM: Artificial Sequence
<220> FEATURE:
<223> OTHER INFORMATION: Synthetic peptide

<400> SEQUENCE: 55

Ala Ile Val Tyr Leu Ile Ala Leu Ala Val Cys Gln Cys Arg Arg Lys
1               5                   10                  15

Asn Tyr Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic peptide

<400> SEQUENCE: 56

Ala Ile Val Tyr Leu Ala Leu Ala Cys Gln Cys Arg Arg Lys Asn Tyr
1               5                   10                  15

Gly

<210> SEQ ID NO 57
<211> LENGTH: 15
<212> TYPE: PRT
<213> ORGANISM: Artificial Sequence
<220> FEATURE:
<223> OTHER INFORMATION: Synthetic peptide

<400> SEQUENCE: 57

Ala Lys Lys Tyr Leu Ala Leu Ala Cys Gln Cys Arg Lys Asn Tyr
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Synthetic peptide

<400> SEQUENCE: 58

Cys Gln Cys Arg Arg Lys Asn Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Asn Lys Arg Arg Cys Gln Cys
```

```
<210> SEQ ID NO 60
<211> LENGTH: 15
<212> TYPE: PRT
<213> ORGANISM: Artificial Sequence
<220> FEATURE:
<223> OTHER INFORMATION: Synthetic peptide

<400> SEQUENCE: 60

Ala Gln Ala Arg Arg Lys Asn Tyr Gly Gln Leu Asp Ile Phe Pro
1               5                   10                  15

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Ala Gln Ala Arg Arg Lys Asn
1               5

<210> SEQ ID NO 62
<211> LENGTH: 69
<212> TYPE: PRT
<213> ORGANISM: Artificial Sequence
<220> FEATURE:
<223> OTHER INFORMATION: Synthetic peptide

<400> SEQUENCE: 62

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
                20                  25                  30

Gly Arg Tyr Val Pro Pro Ser Ser Thr Asp Arg Ser Pro Tyr Glu Lys
            35                  40                  45

Val Ser Ala Gly Asn Gly Gly Ser Ser Leu Tyr Thr Asn Pro Ala Val
        50                  55                  60

Ala Ala Ala Ser Leu
65
```

MUC-1 CYTOPLASMIC DOMAIN PEPTIDES AS INHIBITORS OF CANCER

This application claims benefit of U.S. Provisional Application Ser. No. 61/106,380, filed Oct. 17, 2008, and U.S. Provisional Application Ser. No. 61/177,109, filed May 11, 2009, the entire contents of both applications being hereby incorporated by reference.

BACKGROUND OF THE INVENTION

1. Field of the Invention

This invention relates to regulation of cell growth, and more particularly to regulation of cancer cell growth. In particular, MUC1 peptides derived from a particular region of the MUC1 cytoplasmic domain have been shown to inhibit MUC1 oligomerization and nuclear translocation, causing inhibition and even death of MUC1-expressing tumor cells.

2. Related Art

Mucins are extensively O-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 1 (MUC1) can also signal to the interior of the cell through its cytoplasmic domain. MUC1 has no sequence similarity with other membrane-bound mucins, except for the presence of a sea urchin sperm protein-enterokinase-agrin (SEA) domain (Duraisamy et al., 2006). In that regard, MUC1 is translated as a single polypeptide and then undergoes autocleavage at the SEA domain (Macao, 2006).

The MUC1 N-terminal subunit (MUC1-N) contains variable numbers of tandem repeats with a high proportion of serines and threonines that are modified by O-glycosylation (Siddiqui, 1988). MUC1-N extends beyond the glycocalyx of the cell and is tethered to the cell surface through noncovalent binding to the transmembrane MUC1 C-terminal subunit (MUC1-C) (Merlo, 1989). MUC1-C consists of a 58-amino acid extracellular domain, a 28-amino acid transmembrane domain and a 72-amino acid cytoplasmic domain that interacts with diverse signaling molecules (Kufe, 2008). Shedding of MUC1-N into the protective physical barrier leaves MUC1-C at the cell surface as a putative receptor to transduce intracellular signals that confer growth and survival (Ramasamy et al., 2007; Ahmad et al., 2007).

Available evidence indicates that human carcinomas have exploited MUC1 function in promoting tumorigenicity. In this context, with transformation and loss of polarity, MUC1 is expressed at high levels on the entire cell surface in carcinomas of the breast and other epithelia (Kufe, 1984). Other work has shown that overexpression of MUC1 confers anchorage-independent growth and tumorigenicity (Li et al., 2003a; Raina et al., 2004; Ren et al., 2004; Wei et al., 2005), at least in part through stabilization of β-catenin (Huang et al., 2005). Moreover, consistent with a survival function for normal epithelial cells, overexpression of MUC1 confers resistance of carcinoma cells to stress-induced apoptosis (Ren et al., 2004; Yin and Kufe, 2003; Yin et al., 2004; Yin et al., 2007).

Loss of restriction to the apical membrane allows for the formation of complexes with the epidermal growth factor receptor (EGFR) and coactivation of EGFR-mediated signaling (Li et al., 2001; Ramasamy et al., 2007). Overexpression of MUC1 by carcinoma cells is also associated with accumulation of the MUC1-C in the cytosol and targeting of this subunit to the nucleus (Li et al., 2003b; Li et al., 2003c) and mitochondria (Ren et al., 2004; Ren et al., 2006). Importantly, oligomerization of MUC1-C is necessary for its nuclear targeting and interaction with diverse effectors (Leng et al., 2007). For example, the MUC1-C cytoplasmic domain (MUC1-CD) functions as a substrate for c-Src (Li et al., 2001), c-Abl (Raina et al., 2006), protein kinase Cδ (Ren et al., 2002) and glycogen synthase kinase 3β (Li et al., 1998) and interacts directly with the Wnt pathway effector, β-catenin (Yamamoto et al., 1997; Huang et al., 2005), and the p53 tumor suppressor (Wei et al., 2005). Thus, while oligomerization appears to be important, there has been no direct evidence that interference with MUC1 oligomer formation would have any beneficial effects in tumor cells, much less how this might be accomplished.

SUMMARY OF THE INVENTION

Thus, in accordance with the present invention, there is provided a method of inhibiting a MUC1-positive tumor cell in a subject comprising administering to said subject a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence. The peptide may comprise at least 5 consecutive MUC1 residues, at least 6 consecutive MUC1 residues, at least 7 consecutive MUC1 residues, at least 8 consecutive MUC1 residues and the sequence may more specifically comprise CQCR (SEQ ID NO:54), CQCRR (SEQ ID NO:50), CQCRRR (SEQ ID NO:51), CQCRRRR (SEQ ID NO:52), CQCRRK (SEQ ID NO:4), or CQCRRKN (SEQ ID NO:53). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K. The peptide may comprise all L amino acids, all D amino acids, or a mix of L and D amino acids.

The MUC1-positive tumor cell may be a carcinoma cell, a leukemia cell or a myeloma cell, such as a prostate or breast carcinoma cell. Administering may comprise intravenous, intra-arterial, intra-tumoral, subcutaneous, topical or intraperitoneal administration, or local, regional, systemic, or continual administration. Inhibiting may comprise inducing growth arrest of said tumor cell, apoptosis of said tumor cell and/or necrosis of a tumor tissue comprising said tumor cell. The subject may be a human.

The method may further comprise administering to said subject a second anti-cancer therapy. The second anti-cancer therapy may be surgery, chemotherapy, radiotherapy, hormonal therapy, toxin therapy, immunotherapy, and cryotherapy. The second anti-cancer therapy may be administered prior to said peptide, after said peptide, or at the same time as said peptide. The method may further comprise the step of assessing the expression of MUC1 in a tumor cell of said subject prior to administering said peptide and/or the method may further comprise the step of assessing the effect of said peptide on the expression of MUC1 in a tumor of said subject.

The peptide may be administered at 0.1-500 mg/kg/d, or 10-100 mg/kg/d. The peptide may be administered daily, for example, for 7 days, 2 weeks, 3 weeks, 4 weeks, one month, 6 weeks, 8 weeks, two months, 12 weeks, or 3 months. The peptide may be administered weekly, for example, for 2 weeks, 3 weeks, 4 weeks, 6 weeks, 8 weeks, 10 weeks, or 12 weeks.

In another embodiment, there is provided a pharmaceutical composition comprising (a) a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence, and (b) a pharmaceutically acceptable carrier, buffer or diluent. The peptide may be at least 5, 6, 7 or 8 consecutive MUC1 residues. The peptide may be no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K, or a cell transduction domain, such as an HIV tat cell transduction domain. The peptide may be at least 8 residues in length, and at least two non-adjacent residues from a bridge through their side chains. The bridge may comprise a linker, chemically modified side chains, or hydrocarbon stapling. The linkers may comprise modifications that stabilize an alpha-helical structure of said peptide. The buffer may comprise β-mercaptoethanol, glutathione or ascorbic acid, or other reducing agent that keeps the peptide in a monomeric state.

In yet another embodiment, there is provided a method of inhibiting MUC1-oligomerization and nuclear transport in a cell comprising contacting a MUC1-expressing cell with a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence. The peptide may comprise at least 5 consecutive MUC1 residues, at least 6 consecutive MUC1 residues, at least 7 consecutive MUC1 residues, at least 8 consecutive MUC1 residues, and the sequence may more specifically comprise CQCR, CQCRR, CQCRRR, CQCRRRR, CQCRRK, or CQCRRKN. The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K. The peptide may comprise all L amino acids, all D amino acids, or a mix of L and D amino acids.

The MUC1-expressing cell may be a tumor cell, such as a carcinoma cell, a leukemia cell or a myeloma cell, such as a prostate or breast carcinoma cell. The tumor cell may be located in a living subject. The living subject may be a human subject.

In still yet another embodiment, there is provided a peptide mimetic that mimics the structure and MUC-1 binding capability of a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence. A further embodiment provides for a MUC1 peptide of at least 3 consecutive MUC1 residues and no more than 20 consecutive MUC1 residues and comprising the sequence CQC, wherein all the amino acid residues of said peptide are D-amino acids. The peptide may further comprise the sequence KRRCQC (SEQ ID NO:49).

The cancer cell can be, e.g., a breast cancer, lung cancer, colon cancer, pancreatic cancer, renal cancer, stomach cancer, liver cancer, bone cancer, hematological cancer, neural tissue cancer, melanoma, ovarian cancer, testicular cancer, prostate cancer, cervical cancer, vaginal cancer, or bladder cancer cell.

Also embraced by the invention are methods of killing a cancer cell. The methods can include, before, after, or at the same time as performing the methods described above, exposing the subject to one or more additional therapies. The therapies can be, for example, one or more forms of ionizing radiation and/or one or more chemotherapeutic agents. The one or more chemotherapeutic agents can be, for example, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned. Also contemplated as combination therapies are hormonal therapy, immunotherapy, toxin therapy, cryotherapy and surgery.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

(FIG. 1A)

Schematic representation of the MUC1-C subunit and the 72-amino acid sequence of MUC1-CD are shown. The N-terminal 15 amino acids (shaded sequence) MUC1/CQC and mutated MUC1/AQA peptides were synthesized with the poly-dArg transduction domain. (FIG. 1B) His-MUC1-CD (1.4 mg/ml) was immobilized on a sensor chip in a BIAcore. MUC1/CQC was injected over the chip at 10 μM. Raw binding data were analyzed by BIAevaluation software version 3.0 and fit to a 1:1 Languir binding model. (FIG. 1C) Purified His-MUC1-CD (1.5 mg/ml) was incubated with PBS, 200 μM MUC1/CQC or 200 μM MUC1/AQA for 1 h at room temperature. The proteins were separated in a non-reducing SDS-polyacrylamide gel and analyzed by immunoblotting with anti-MUC1-C. (FIG. 1D) 293 cells were transiently transfected to express an empty vector or GFP-MUC1-CD and Flag-MUC1-CD. At 48 h after transfection, the cells were treated with 5 µM MUC1/CQC or MUC1/AQA for 3 d. The cells were then harvested for immunoblotting with anti-MUC1-C (left panel). Whole cell lysates were also precipitated with anti-Flag and the precipitates were immurioblotted with the indicated antibodies (right panels). ED-MUC1 ectodomain; TM-MUC1 transmembrane; CD-MUC1 cytoplasmic domain.

(FIG. 2A) ZR-75-1 cells were incubated with 5 µM FITC-labeled MUC1/CQC peptide for the indicated times and then analyzed by flow cytometry. The mean fluorescence index (MFI) is included in each of the panels. (FIGS. 2B-C) ZR-75-1 (FIG. 2B) and MCF-7 (FIG. 2C) cells were incubated in the presence of 5 µM MUC1/CQC or MUC1/AQA peptide for 3 d. Whole cell lysates (WCL) (left panels) and nuclear lysates (right panels) were immunoblotted with the indicated antibodies.

(FIG. 4A) ZR-75-1 cells were stably infected with an empty lentivirus (vector) or one expressing a MUC1 siRNA. Lysates for the infected cells were immunoblotted with the indicated antibodies. (FIG. 4B) ZR-75-1/vector cells were left untreated (diamonds), and ZR-75-1/vector (squares) and ZR-75-1/MUC1siRNA (triangles) cells were treated with 5 µM MUC1/CQC peptide for the indicated times, Viable cell number was determined by trypan blue exclusion. (FIG. 4C) 293 cells were left untreated (diamonds), and treated with 5 µM MUC1/CQC (squares) or MUC1/AQA (triangles) for the indicated times. Viable cell number was determined by trypan blue exclusion. (FIG. 4D) MCF-10A cells were left untreated (left panel), and treated with 5 µM MUC1/CQC (middle panel) or MUC1/AQA (right panel). At 3 d, cells were analyzed for cell cycle distribution. (FIG. 4E) MCF-10A cells were left untreated (diamonds), and treated with 5 µM MUC1/CQC (squares) or MUC1/AQA (triangles) for the indicated times. Viable cell number was determined by trypan blue exclusion.

(FIG. 5A) Four to six week-old female Balb-c nu/nu mice were implanted with 17-β-estradiol plugs. After 24 h, ZR-75-1 breast cancer cells (imbedded in matrigel) were injected subcutaneously in the flank. When tumors were ~150 mm$^3$, the mice were paired matched into groups and injected intraperitoneally with PBS (vehicle control; closed squares), 50 mg/kg MUC1/AQA peptide (control peptide; open squares) or 10 mg/kg MUC1/CQC peptide (closed triangles) daily for 21 d. Another group was treated with 50 mg/kg MUC1/CQC peptide daily (↑) for 6 d (open triangles). Mice were weighed twice weekly and tumor measurements were performed every 4 d. (FIGS. 5B and 5C). On day 24 (asterisk), tumors harvested from the control group and the group treated with 50 mg/kg/dx6d were stained with H&E (FIG. 5B) and with an antibody against MUC1 (FIG. 5C).

(FIG. 6A) Mice were injected with ZR-75-1 cells as described in the legend to FIG. 5A. When tumors were ~275 mm$^3$, the mice were paired matched into groups and injected intraperitoneally with PBS (vehicle control; open squares) or 30 mg/kg MUC1/CQC peptide (closed squares) daily for 21 days (solid horizontal bar). The control mice were sacrificed on day 32 when tumors reached ~1200 mm$^3$. The treated mice were monitored until day 52 when tumors were harvested for H&E staining (FIG. 6B).

FIG. 8. Sequences of MUC1-CD Stapled Peptides. S5 and B5 in GO-200-1B and GO-200-2B represent bridge connections.

FIG. 13. Effect of different MUC1-CD CQC-region peptides on the growth of triple negative breast carcinoma cells. MDA-MB-231 triple-negative breast carcinoma cells were treated with 5 µM of different MUC1-CD CQC-region peptides for 6 days. Viable cell number on day 6 was determined by trypan blue exclusion. The results demonstrate that treatment of MDA-MB-231 cells with different peptides was associated with significant inhibition of growth. Y-axis represents relative growth as compared to control untreated cells.

DESCRIPTION OF ILLUSTRATIVE EMBODIMENTS

I. The Present Invention

Figure 1A:
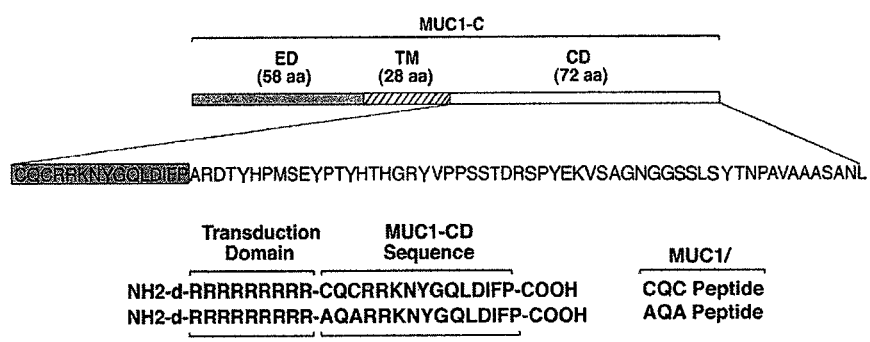
FIGS. 1A-D. MUC1/CQC peptide blocks MUC1 oligomerization.

MUC1 has been studied extensively by the inventors and others for its role in cancer. As discussed above, human MUC1 is heterodimeric glycoprotein, translated as a single polypeptide and cleaved into N- and C-terminal subunits in the endoplasmic reticulum (Ligtenberg et al., 1992; Macao et al., 2006; Levitin et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anti-cancer agents (Yin and Kufe, 2003; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 3β, c-Src, protein kinase Cδ, and c-Abl (Raina et al., 2006; Li et al., 1998; Li et al., 2001; Ren et al., 2002).

The mechanisms responsible for nuclear targeting of MUC1-C are unclear. Proteins containing a classical nuclear localization signal (NLS) are imported into the nucleus by first binding to importin α and then, in turn, importin β (Weis, 2003). The cargo-importin α/β complex docks to the nuclear pore by binding to nucleoporins and is transported through the pore by a mechanism dependent on the Ran GTPase. Classical NLSs are monopartite with a single cluster of 4-5 basic amino acids or bipartite with two clusters of basic amino acids separated by a linker of 10-12 amino acids. MUC1-CD contains a RRK motif that does not conform to a prototypical monopartite NLS (Hodel et al., 2002). However, certain proteins containing non-classical NLSs are transported through the nuclear pore by binding directly to importin β (Kau et al., 2004). Importin β associates with several nucleoporins (Ryan and Wente, 2000), including Nup62, which is located on both the cytoplasmic and nucleoplasmic faces of nuclear pore complexes (Percipalle et al., 1997). Other studies have indicated that β-catenin is imported into the nucleus by an importin- and nucleoporin-independent mechanism (Suh and Gumbiner, 2003).

In 2006, the inventors reported that MUC1 is imported into the nucleus by a mechanism involving binding to Nup62. They also demonstrated that MUC1 forms oligomers through a CQC motif in the MUC1 cytoplasmic domain and that MUC1 oligomerization is necessary for nuclear import. Here, they have extended this work to encompass a further understanding of the role that the CQC motif plays in oligomer formation. They also have demonstrated that short peptides corresponding to this region are able to disrupt MUC1 oligomer formation, preventing transport into the nucleus of tumor cells. These peptides are able to inhibit tumor cell growth, as well as induce apoptosis in such cells and even necrosis of tumor tissue. These and other aspect of the invention are described in detail below.

II. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20-amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58-amino acid extracellular region, a 28-amino acid transmembrane domain and a 72-amino acid cytoplasmic domain (CD; SEQ ID NO:1) (Merlo et al., 1989). The human MUC1 sequence is shown below:

(SEQ ID NO: 2)
GSVVVQLTLAFREGTINVHDVETQFNQYKTEAASRYNLTISDVSVSDVPF

PFSAQSGAGVPGWGIALLVLVCVLVALAIVYLIALAVCQCRRKNYGQLDI

FPARDTYHPMSEYPTYIITHGRYVPPSSTDRSPYEKVSAGNGGSSLSYTN

PAVAATSANL

The bold sequence indicates the CD, and the underlined portion is an oligomer-inhibiting peptide (SEQ ID NO:3) described in the examples.

With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

B. Function

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al. 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

III. MUC1 Peptides

A. Structure

The present invention contemplates the design, production and use of various MUC1 peptides. The structural features of these peptides are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may also include the CQCR motif, CQCRR motif and the CQCRRK motif. Thus, the peptides will have, at a minimum, these three consecutive residues of the MUC1-C domain. Third, the peptides will have at least one amino acid residue attached to the NH$_2$-terminal side of the first C residue in the CQC motif, such that the first C residue is "covered" by that at least one amino acid attached thereto. This residue may be native to MUC1 (i.e., from the transmembrane domain), may be selected at random (any of the 20 naturally-occurring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 5-50 residues, 6-50 residues, 7-50 residues, 7-25, residues, 4-20 residues, 5-20 residues, 6-20 residues, 7-20 residues, and 7-15 residues are contemplated. The number of consecutive MUC1 residues may be 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues and 4-15 residues, 5-15, residues, 6-15 residues or 7-15 residues are contemplated.

The present invention may utilize an L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

TABLE 1

| CDD/CTD PEPTIDES | SEQ ID NO |
| --- | --- |
| QAATATRGRSAASRPTERPRAPARSASRPRRPVE | 5 |
| RQIKIWFQNRRMKWKK | 6 |
| RRMKWKK | 7 |
| RRWRRWWRRWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKIK | 14 |
| GWTLNSAGYLLGKINLKALAALAKXIL | 15 |
| LLILLRRRIRKQANAHSK | 16 |
| SRRHHCRSKAKRSRHH | 17 |

TABLE 1-continued

| CDD/CTD PEPTIDES | SEQ ID NO |
|---|---|
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., *Journal of the American Chemical Society*, 2000. 122 (24): p. 5891-5892.

D. Design, Variants and Analogs

The present invention focuses on peptides comprising the sequence CQC. Having identified this key structure in MUC1 oligomer formation, the inventors also contemplate that variants of the CQC sequence may be employed. For example, certain non-natural amino acids that satisfy the structural constraints of the CQC sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography. X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy. Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cell that expresses MUC1, and more particularly, that overexpresses MUC1. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

Peptides or analogs that inhibit MUC1 oligomer formation are generally useful as anti-cancer therapeutics or prophylactics. They can be administered to mammalian subjects (e.g., human breast cancer patients) alone or in conjunction with other drugs and/or radiotherapy. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for MUC1 expression (MUC1 protein or MUC1 mRNA expression) by methods known in the art. In this way, subjects can be identified as having a MUC1-expressing or overexpressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

V. Combination Therapies

Tumor cell resistance to DNA damaging agents represents a major problem in clinical oncology. One goal of current cancer research is to find ways to improve the efficacy of chemo- and radiotherapy. One way is by combining such traditional therapies with gene therapy. In the context of the present invention, it is contemplated that MUC1 peptide therapy could be used similarly in conjunction with chemotherapeutic, radiotherapeutic, or immunotherapeutic intervention.

To kill cells, inhibit cell growth, inhibit metastasis, inhibit angiogenesis or otherwise reverse or reduce the malignant phenotype of tumor cells, using the methods and compositions of the present invention, one would generally contact a target cell with a MUC1 peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the MUC1 peptide and the other includes the agent.

Alternatively, the MUC1 treatment may precede or follow the other treatment by intervals ranging from minutes to weeks. In embodiments where the other treatment and the MUC1 peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 peptide or the other therapy will be desired. Various combinations may be employed, where the MUC1 peptide is "A," and the other therapy is "B," as exemplified below:

| A/B/A | B/A/B | B/B/A | A/A/B | B/A/A |
|---|---|---|---|---|
| A/B/B | B/B/B/A | B/B/A/B | A/A/B/B | A/B/A/B |
| A/B/B/A | B/B/A/A | B/A/B/A | B/A/A/B | B/B/B/A |
| A/A/A/B | B/A/A/A | A/B/A/A | A/A/B/A | A/B/B/B |
| B/A/B/B | B/B/A/B | | | |

Other combinations are contemplated. Again, to achieve cell killing, both therapies are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of MUC1 peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining MUC1 therapies with chemo- and radiotherapies, it also is contemplated that combination with immunotherapy, hormone therapy, toxin therapy and surgery. In particular, one may employ targeted therapies such as Avastin, Erbitux, Gleevec, Herceptin and Rituxan.

It also should be pointed out that any of the foregoing therapies may prove useful by themselves in treating cancer.

VI. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture. Human breast cancer ZR-75-1, ZR-75-1/vector, ZR-75-1/MUC1 siRNA (Ren et al., 2004) cell lines were grown in RPMI1640 medium supplemented with 10% heat-inactivated fetal bovine serum (HI-FBS), 100 U/ml penicillin, and 100 µg/ml streptomycin (Invitrogen) in a humidified incubator at 37° C. and 5% $CO_2$. Human MCF-7 breast cancer cells and 293 cells were grown in Dulbecco's modified Eagle's medium with 10% HI-FBS, antibiotics and 2 mM L-glutamine. Human MCF-10A breast epithelial cells were grown in mammary epithelial cell growth medium (MEGM; Lonza). Cells were treated with the MUC1/CQC or MUC1/AQA peptides synthesized by the MIT Biopolymer Laboratory, Cambridge, Mass. Viability was determined by trypan blue exclusion.

Immunoprecipitation and Immunoblot Analysis. Whole cell and nuclear lysates were prepared as described (Leng et al., 2007). Soluble proteins were subjected to immunoprecipitation with anti-Flag (Sigma, St. Louis, Mo.). Immunoprecitates and soluble proteins were analyzed by immunoblotting with anti-His (Cell Signaling Technology, Danvers, Mass.), anti-GFP (Millipore, Danvers, Mass.), anti-Flag, anti-MUC1-C (Abl; NeoMarkers, Fremont, Calif.), anti-lamin B (EMD, La Jolla, Calif.) or anti-β-actin (Sigma). Reactivity was detected with horseradish peroxidase-conjugated second antibodies and chemiluminescence.

Cell Transfection. 293 cells were transfected with vectors expressing GFP, GFP-MUC1-CD or Flag-MUC1-CD in the presence of Lipofectamine as described (Leng et al., 2007).

Peptide Uptake. Cells were incubated with FITC-labeled MUC1/CQC peptide (MIT Biopolymer Laboratory), washed with cold PBS, fixed in 1% paraformaldehyde/PBS and analyzed for fluorescence by flow cytometry.

Analysis of Cell Cycle Distribution, Apoptosis and Necrosis. Cells were harvested, washed with PBS, fixed with 80% ethanol, and incubated in PBS containing 40 µg/ml RNAse and 40 µg/ml propidium iodide for 30 min at 37° C. Cell cycle distribution was determined by flow cytometry. Sub-G1 DNA content was assessed by staining ethanol-fixed and citrate buffer-permeabilized cells with propidium iodide and monitoring by flow cytometry as described (Yin et al., 2007). For assessment of necrosis, cells were incubated with 1 µg/ml propidium iodide/PBS for 5 min at room temperature and then monitored by flow cytometry as described (Yin et al., 2007).

Human Breast Tumor Xenograft Model. Balb-c nu/nu female mice (Charles River Laboratories, Wilmington, Mass.), 4-6 weeks old weighing 18-22 grams, were implanted subcutaneously with 17-β-estradiol plugs (0.72 mg; Innovative Research, Sarasota, Fla.) using a trocar gun. After 24 h, $1\times10^7$ ZR-75-1 cells imbedded in Matri-Gel (BD Biosciences) were injected subcutaneously in the flank. When tumors were detectable at ~150 mm$^3$ (Cohort I) or 275 mm$^3$ (Cohort 2), the mice were pair matched into treatment and control groups. Each group contained 5 mice, each of which was ear tagged and followed throughout the study. Initial dosing was administered at the time of pair matching (day 1). Phosphate-buffered saline (vehicle), MUC1/CQC peptide and MUC1/AQA peptide were administered daily by intraperitoneal injection. Mice were weighed twice weekly, and tumor measurements were performed using calipers every 4 d. Tumor volume (V) was calculated using the formula V=W2×L/2, where W and L are the smaller and larger diameters, respectively. At sacrifice, the mice were perfused with saline and then phosphate-buffered formalin by cardiac administration. Tumors were excised, immersion fixed for 4 h, dehydrated through a graded series of ethanols, and processed for routine paraffin embedding. Tumors were evaluated by H&E staining and for immunoperoxidase staining with anti-MUC1 as described (Kufe, 1984).

Drugs and cytokines. Cisdiaminedichloroplatinum (II), Doxorubicin (adriamycin), Taxol (Paclitaxel) were purchased from Sigma (St. Louis, Mo.). rh-TNF-alpha was purchased from Promega (Madison, Wis.). GO-203 peptide was synthesized by Anaspec Inc.

In vitro cytotoxicity and combination assays. Cells were seeded in a 96-well flat-bottomed microtiter plate (Fisher) at 1000 cells per well for a 6-day experiment or at 3000 cells per well for a 3-day experiment. The cells were then cultured for 24 h. Anti-cancer drugs and GO-203 were diluted to the indicated concentrations and added to the cells. GO-203 (5 µmol/L) was added every 24 h for 72 h. Cell viability was determined by adding MTS reagent to the cells and reading the absorbance at 490 nm by a microplate reader.

Data analysis. The IC$_{50}$ values for all the anti-cancer drugs were determined by non-linear regression analysis using Graphpad Prism (GraphPad Software, San Diego CA). The CombiTool computer program (version 2.001, IMB Jena Biocomputing Group) was used to calculate the combination index within a dose range in the presence of 5 µmol/L GO-203.

Example 2

Results

Figure 1B:
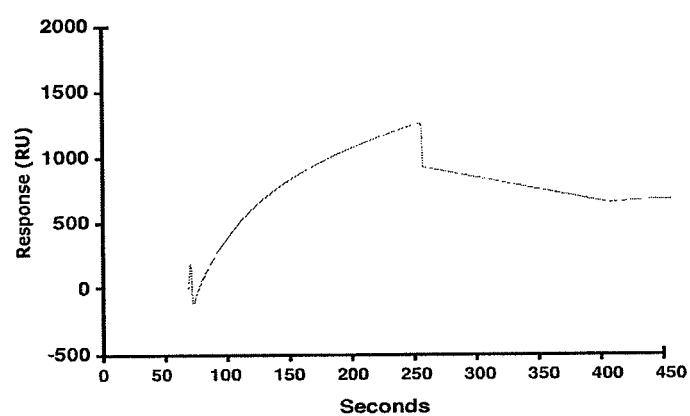
Figure 1C:
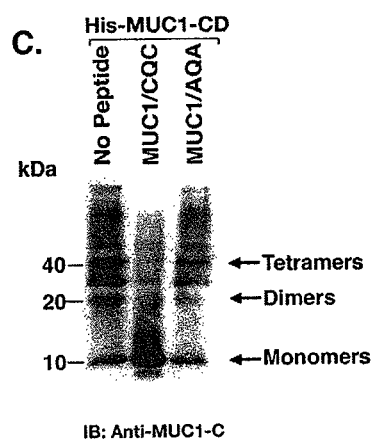
Figure 1D:
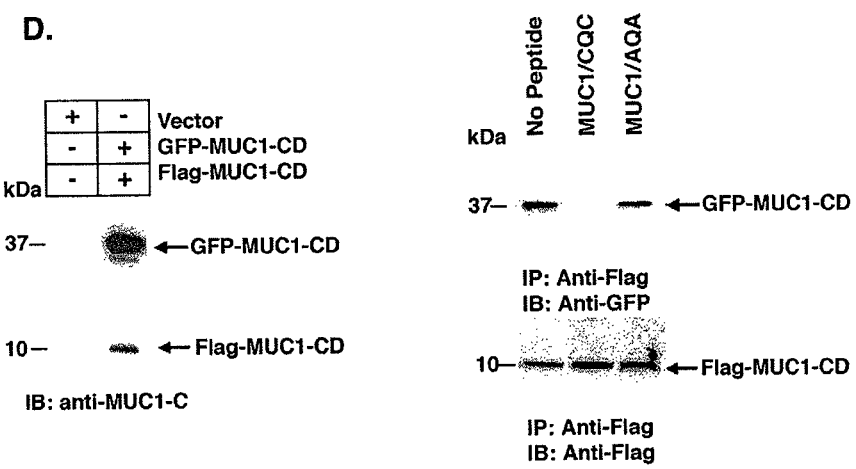

Effects of the MUC1/CQC peptide on MUC1 oligomer formation. The MUC1 cytoplasmic domain (MUC1-CD) contains a CQC motif that is necessary for the formation of oligomers and nuclear localization (Leng et al., 2007). To determine whether a small molecule can be designed to block oligomerization, the inventors synthesized a peptide derived from the N-terminal region of MUC1-CD that contains the CQC motif (MUC1/CQC peptide; FIG. 1A). A poly D-arginine transduction domain was included in the synthesis to facilitate entry of the peptide into cells (Fischer, 2007) (FIG. 1A). As a control, a similar peptide was synthesized in which the CQC motif was altered to AQA (MUC1/AQA peptide; FIG. 1A). To assess binding of the peptides to MUC1-CD, the inventors immobilized His-tagged MUC1-CD to a BIAcore sensor chip. The MUC1/CQC peptide bound to His-MUC1-CD with a dissociation constant (Kd) of 30 nM (FIG. 1B), which is similar to that obtained with MUC1-CD oligomers (Leng et al., 2007). By contrast, there was no apparent binding of the MUC1/AQA peptide (data not shown). Purified His-tagged MUC1-CD forms oligomers as detected by electrophoresis in polyacrylamide gels (FIG. 1C). Incubation of His-MUC1-CD with the MUC1/CQC peptide substantially decreased oligomer formation and increased the monomers (FIG. 1C). Moreover, incubation with the MUC1/AQA peptide had little if any effect (FIG. 1C). To assess effects on MUC1 oligomerization in vivo, 293 cells were transfected with vectors expressing GFP-MUC1-CD and Flag-MUC1-CD (FIG. 1D, left). Complexes of GFP-MUC1-CD and Flag-MUC1-CD were detectable by coprecipitation of lysates from cells not exposed to peptide (FIG. 1D, right). In concert with the in vitro results, incubation of the transfected 293 cells with MUC1/CQC peptide was associated with disruption of the interaction between Flag-MUC1-CD and GFP-MUC1-CD (FIG. 1D, right). In addition, the MUC1/AQA peptide had no apparent effect (FIG. 1D, right). These results indicate that the MUC1/CQC peptide binds to MUC1-CD and blocks formation of MUC1-CD oligomers in vitro and in cells.

Figure 2A:
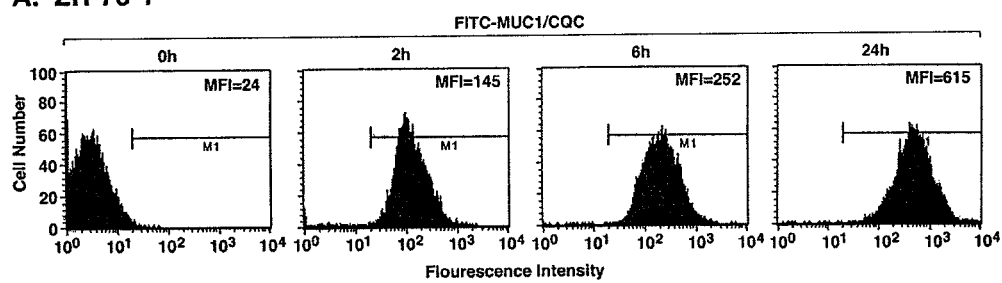
FIGS. 2A-C. MUC1/CQC peptide blocks nuclear localization of MUC1-C.
Figure 2B:
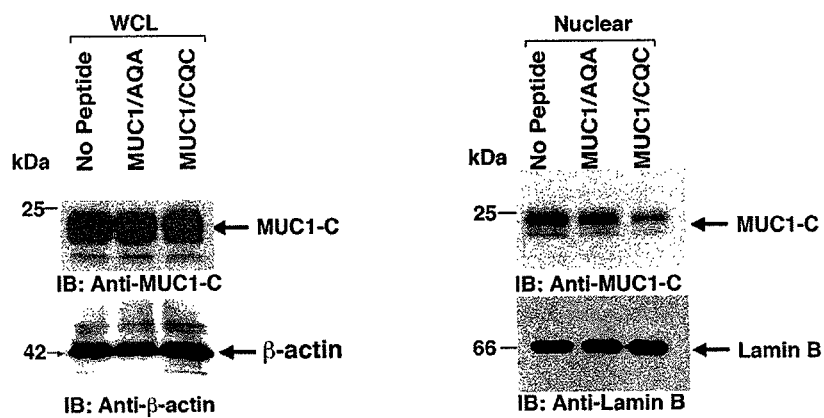
Figure 2C:
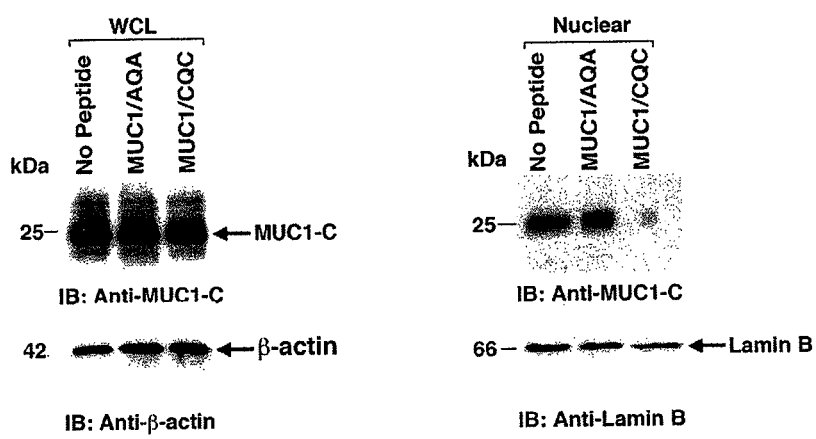

MUC1/CQC peptide blocks targeting of MUC1-C to the nucleus. Human ZR-75-1 and MCF-7 breast cancer cells overexpress endogenous MUC1, and thus represent potential models for evaluating effects of the MUC1/CQC peptide (Ramasamy et al., 2007). To assess uptake, the ZR-75-1 cells were incubated with 5 µM FITC-MUC1/CQC peptide (FIG. 2A). At 2 h, analysis of the cells by flow cytometry showed a substantial increase in fluorescence intensity with a mean (MFI) of 145 (FIG. 2A). Further increases in MFI were identified at 6 and 24 h (FIG. 2A). Oligomerization of MUC1-C is necessary for its nuclear import (Leng et al., 2007). Treatment of ZR-75-1 cells with the MUC1/CQC or the MUC1/AQA peptide had no effect on cellular MUC1-C levels (FIG. 2B). However, in concert with effects on oligomerization, treatment with the MUC1/CQC, and not the MUC1/AQA, peptide was associated with decreases in nuclear MUC1-C levels (FIG. 2B). Similar effects were observed in MCF-7 cells with down-regulation of nuclear MUC1-C levels in response to treatment with the MUC1/CQC peptide (FIG. 2C). These findings indicate that the MUC1/CQC peptide blocks MUC1-C oligomerization and thereby targeting of MUC1-C to the nucleus.

Figure 3A:
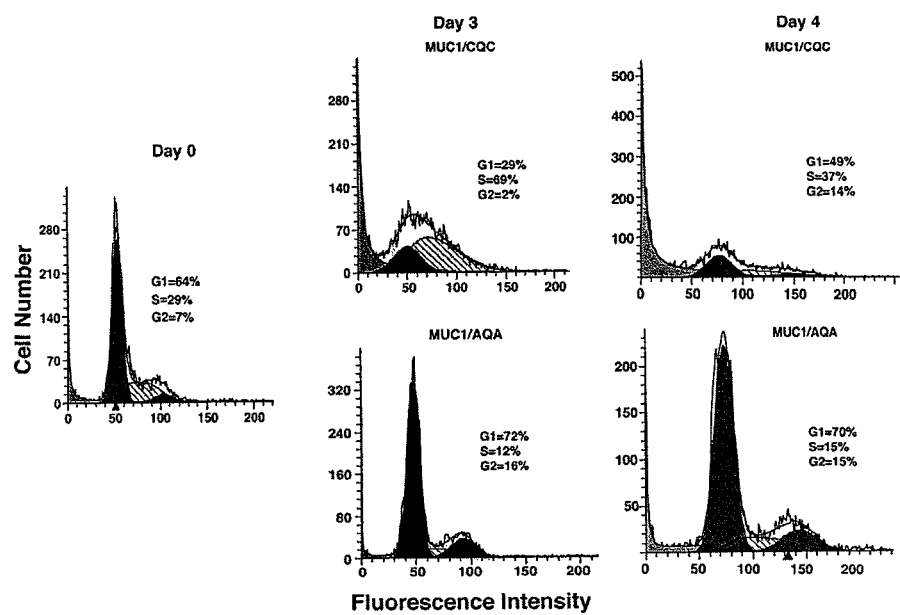
FIGS. 3A-D. MUC1/CQC peptide induces S phase arrest and necrosis. ZR-75-1 (FIGS. 3A-B) and MCF-7 (FIGS. 3C-D) cells were treated with 5 µM MUC1/CQC or MUC1/AQA for 3 and 4 d. Cells were fixed and analyzed for cell cycle distribution by flow cytometry (FIGS. 3A and 3C). The percentage of cells in G1, S and G2/M phases is included in the panels. Cells were also stained with propidium iodide and analyzed by flow cytometry for necrosis (FIGS. 3B and 3D). The percentage of necrotic cells is included in the panels.

MUC1/CQC peptide blocks growth and induces necrosis. To determine whether the MUC1/CQC peptide affects growth, ZR-75-1 cells were treated with 5 µM MUC1/CQC for 72 h and monitored for cell cycle distribution. Significantly, there was a substantial arrest in S phase as compared to that in cells left untreated or treated with the MUC1/AQA peptide (FIG. 3A). By 96 h, the S phase population was decreased, potentially through attrition by cell death (FIG. 3A). There was little if any accumulation of cells with sub-G1

Figure 3B:
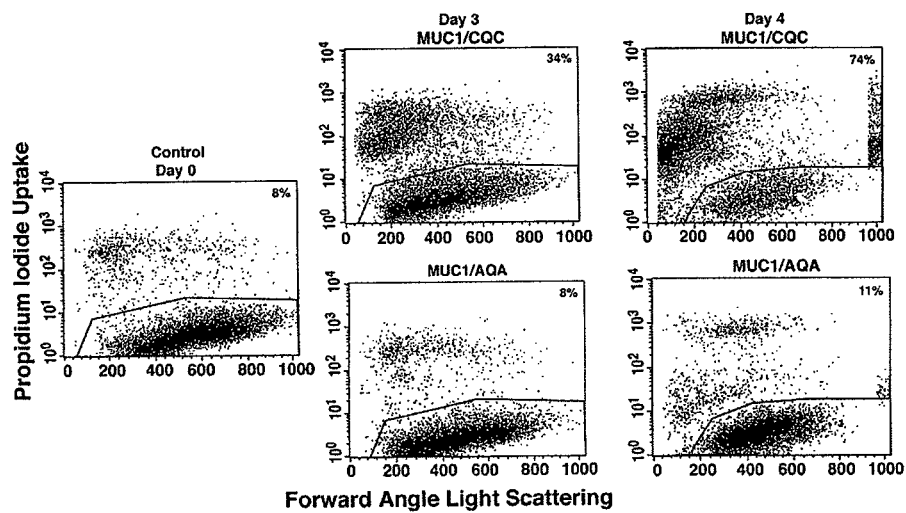
Figure 3C:
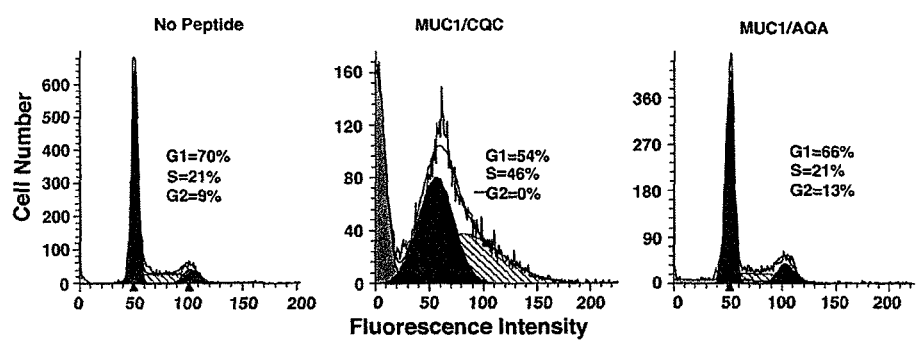
Figure 3D:
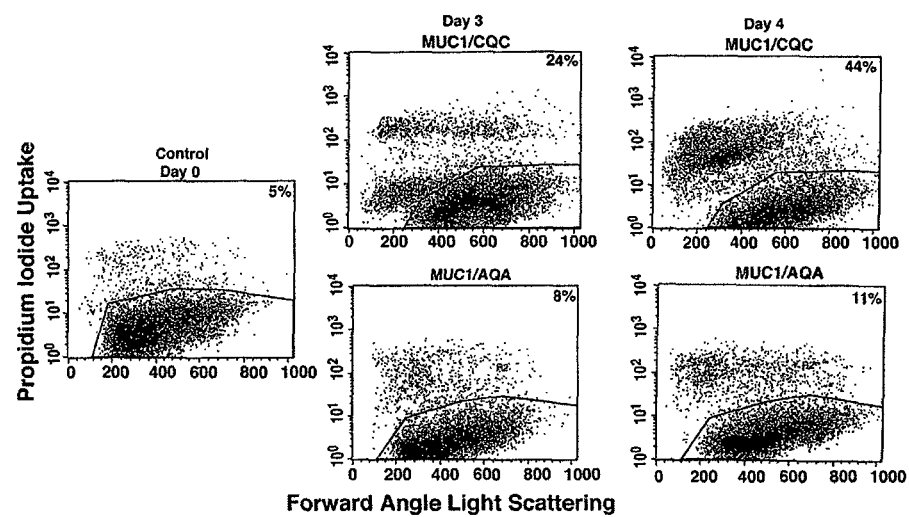

DNA content to support the induction of apoptosis (FIG. 3A). However, treatment of ZR-75-1 cells with the MUC1/CQC, and not the MUC1/AQA, peptide was associated with the induction of necrosis, which was detectable at 72 h and more prominent at 96 h (FIG. 3B). The MCF-7 cells responded similarly to the MUC1/CQC peptide with arrest of growth in S phase (FIG. 3C) and the induction of necrosis (FIG. 3D). These findings indicate that the MUC1/CQC peptide inhibits growth and induces necrosis of human breast cancer cells.

Figure 4A:
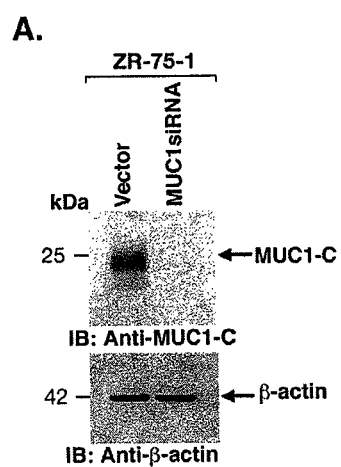
FIGS. 4A-E. Selectivity of MUC1/CQC for MUC1 expressing breast cancer cells.
Figure 4B:
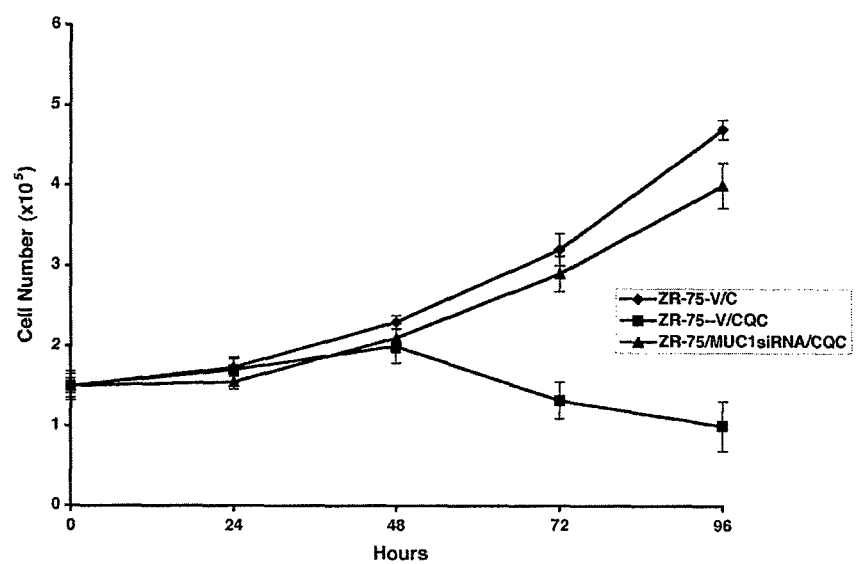
Figure 4C:
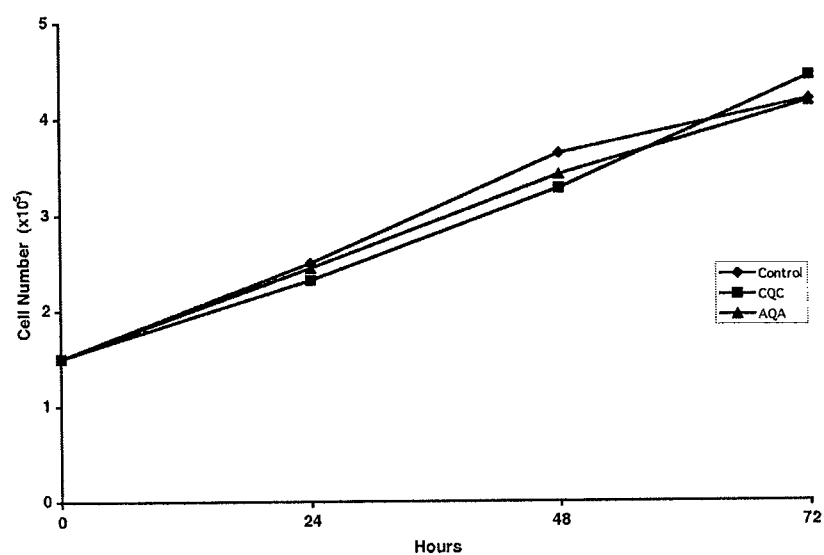
Figure 4D:
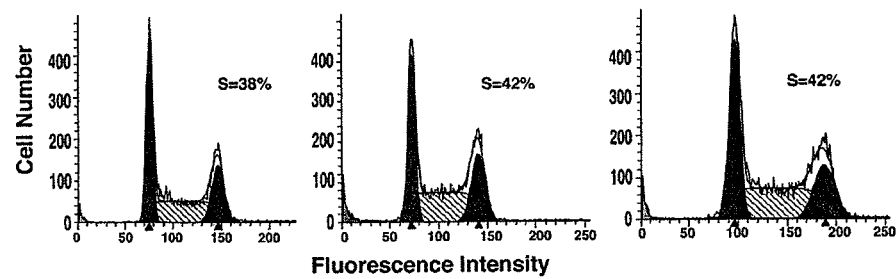
Figure 4E:
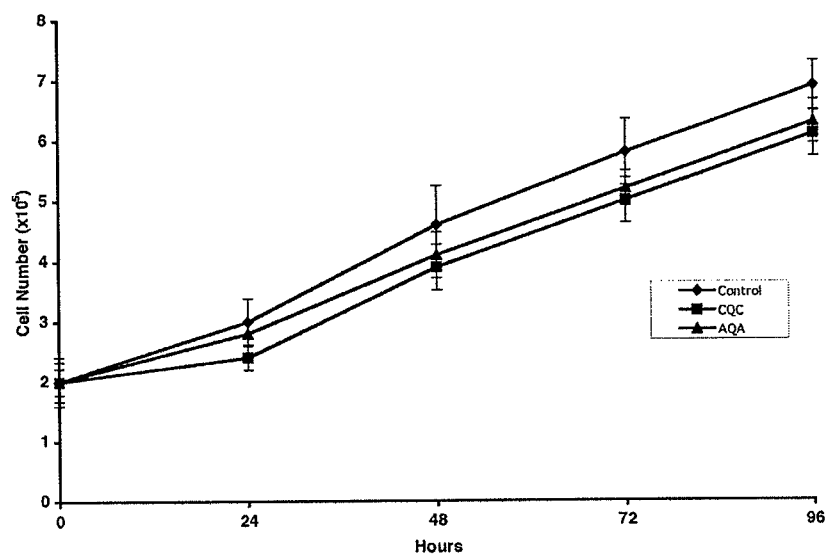

Specificity of MUC1/CQC peptide for MUC1 expressing carcinoma cells. To determine whether the MUC1/CQC peptide has selective activity against breast carcinoma cells that overexpress endogenous MUC1, the inventors treated ZR-75-1 cells that are stably silenced for MUC1 expression with a MUC1siRNA (FIG. 4A). In contrast to growth arrest and death of the control ZR-75-1/vector cells, the MUC1/CQC peptide had substantially less effect on the ZR-75-1/MUC1 siRNA cells (FIG. 4B). In addition, the MUC1/CQC peptide had no apparent effect on growth of MUC1-negative 293 cells (FIG. 4C). Studies were also performed on the MCF-10A non-transformed mammary epithelial cell line (Muthuswamy, 2001; Soule, 1990), which expresses MUC1, but at levels lower than that found in ZR-75-1 and MCF-7 cells (Ahmad et al., 2007). Notably, in contrast to ZR-75-1 and MCF-7 cells, the MUC1/CQC peptide had no effect on MCF-10A cell cycle distribution (FIG. 4D) and growth (FIG. 4E). These findings indicate that the MUC1/CQC peptide has selective activity against breast carcinoma cells that overexpress endogenous MUC1.

Figure 5A:
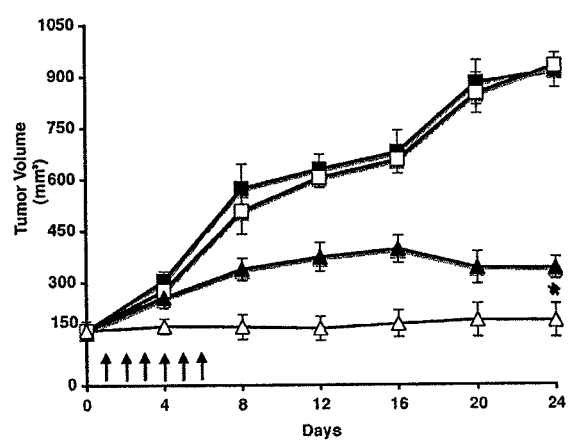
FIGS. 5A-C. MUC1/CQC peptide blocks growth of ZR-75-1 breast tumor xenografts.
Figure 5B:
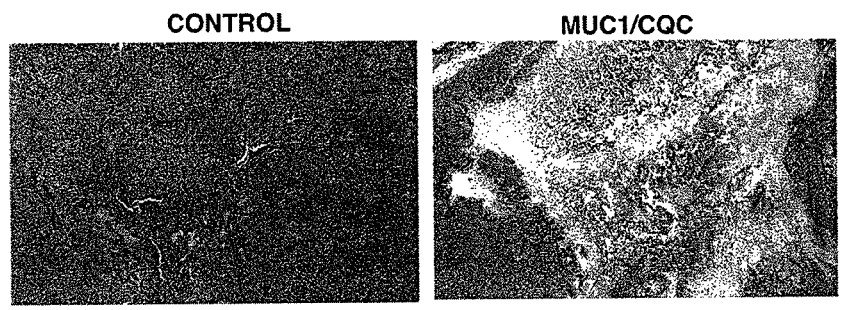
Figure 5C:
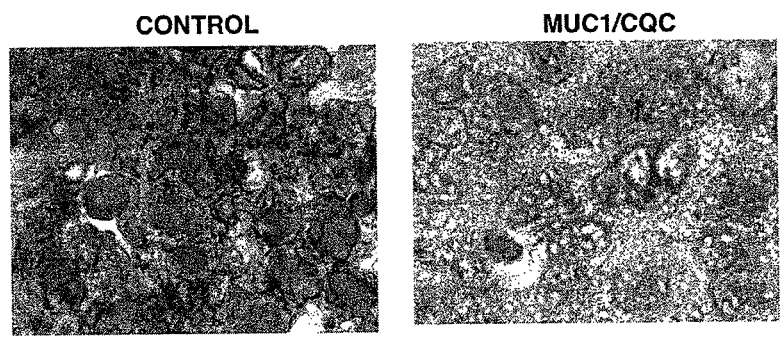

MUC1/CQC peptide inhibits tumorigenicity in vivo. To determine if administration of the MUC1/CQC peptide is associated with effects on body weight, five female nude (nu/nu) mice were injected intraperitoneally (IP) once each day at a dose of 50 mg/kg. Administration of the peptide over 11 d had no apparent effect on weight of the individual mice. Moreover, there was no subsequent effect on bodyweight over the next 28 d after stopping MUC1/CQC administration (data not shown). To assess anti-tumor activity, ZR-75-1 cells ($1\times10^7$) were implanted subcutaneously into the flanks of nude mice. After 12 d, mice bearing tumors of approximately 150 mm$^3$ were treated with the MUC1/CQC peptide at doses of 10 and 50 mg/kg/d. As controls, mice were treated with vehicle alone or with the MUC1/AQA peptide. Administration of the MUC1/CQC peptide at 10 mg/kg/d×21 d slowed growth as compared to that obtained with the MUC1/AQA peptide given at 50 mg/kg/d (FIG. 5A). In addition, administration of the MUC1/CQC peptide at 50 mg/kg/d blocked growth over the initial 7 d of treatment (FIG. 5A). Consequently, treatment was stopped and the mice were monitored for regrowth. Significantly, there was no detectable growth of the tumors over the next 17 d (FIG. 5A). To assess in part the basis for the activity, tumors harvested from control and treated mice were examined by histopathology. Tumors from the MUC1/CQC (10 and 50 mg/kg) treated mice were markedly necrotic compared to that from mice treated with the vehicle or MUC1/AQA peptide (FIG. 5B and data not shown). Notably, however, tumor cells were also detectable around the areas of necrosis (FIG. 5B). Sections of the tumors were also stained with an antibody against MUC1. Treatment with the MUC1/CQC peptide was associated with a marked down-regulation of MUC1 expression compared to that in control tumors and those treated with the MUC1/AQA peptide (FIG. 5C and data not shown).

Figure 6A:
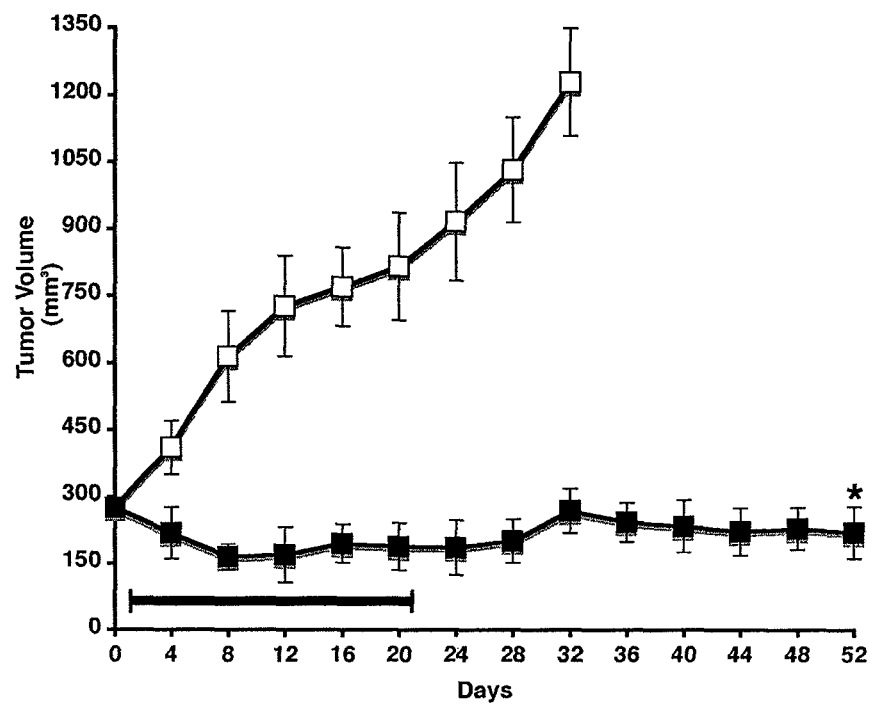
FIGS. 6A-B. Prolonged effects of the MUC1/CQC peptide on ZR-75-1 tumors.
Figure 6B:
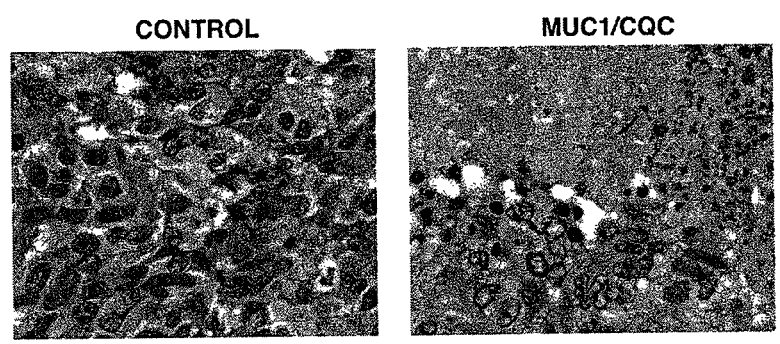
Figure 7:
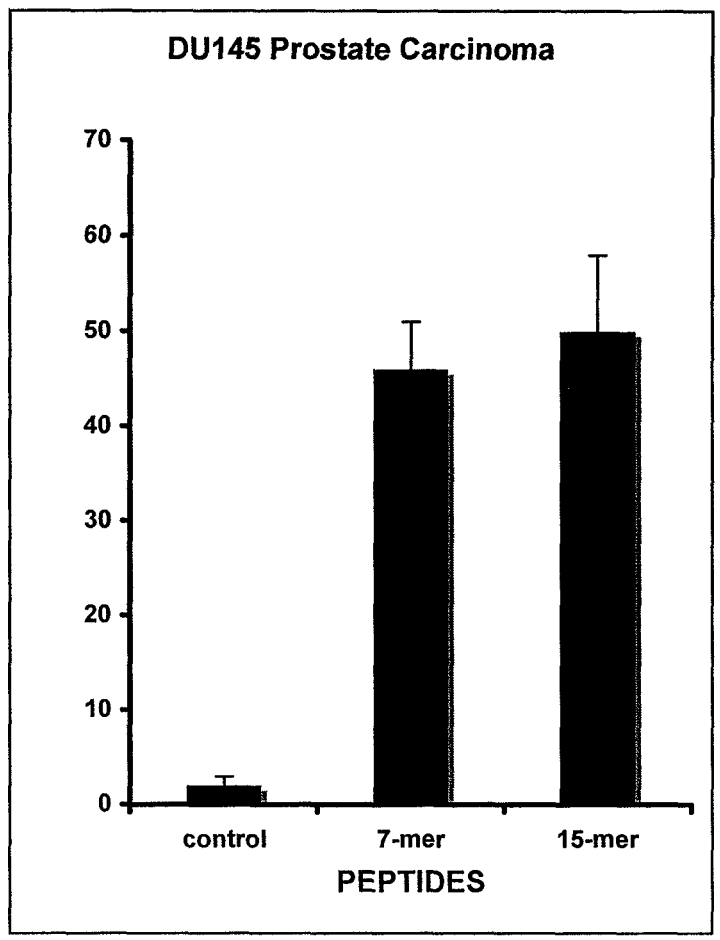
FIG. 7, MUC1 7-mer inhibits prostate carcinoma. DU145 prostate carcinoma cells were treated with 5 µM CQC short (7-mer) or 5 µM CQC long (15-mer) peptides for 4 days. Cell growth was measured by MTT assay. The Y-axis represents percent growth inhibition compared to untreated cells (control).

Studies were also performed on larger tumors (~275 mm$^3$) (FIG. 6A). Administration of the MUC1/CQC peptide at an intermediate dose of 30 mg/kg/d×21 d was associated with arrest of tumor growth (FIG. 6A). Moreover, there was no apparent regrowth over the next 31 d after treatment (FIG. 6A), further indicating that the MUC1/CQC peptide is effective in arresting tumor growth. Tumors harvested on day 52 exhibited the extensive areas of necrosis (FIG. 6B) and down-regulation of MUC1 expression. These findings indicate that the MUC1/CQC peptide down-regulates MUC1 expression and is associated with induction of necrosis and prolonged arrest of tumor growth.

MUC1-C-terminal CQC Stapled Peptides. The intracellular protein-protein interactions that govern many biological pathways are frequently mediated by α-helix structures of proteins. Helical peptides can also interfere with or stabilize protein-protein interactions. Native helical peptides have major shortcomings as therapeutic agents because of low potency, instability and inefficient delivery to cells. Recent studies have shown that these problems could be overcome by a chemical modification of α-helical peptides termed as hydrocarbon stapling.

The inventors used MUC1-C terminal endogenous peptide sequence (AIVYLIALAVCQCRRKNYG) and generated two α-helical peptides, GO-200-1B and GO-200-2B using hydrocarbon stapling:

GO-200-1B:   Ac-AIVYL-*S5*-ALA-*S5*-CQCRRKNYG-NH$_2$

GO-200-2B:   Ac-AKKYL-*S5*-ALA-*B5*-CQC-*S5*-RKNY-NH$_2$

Figure 9A:
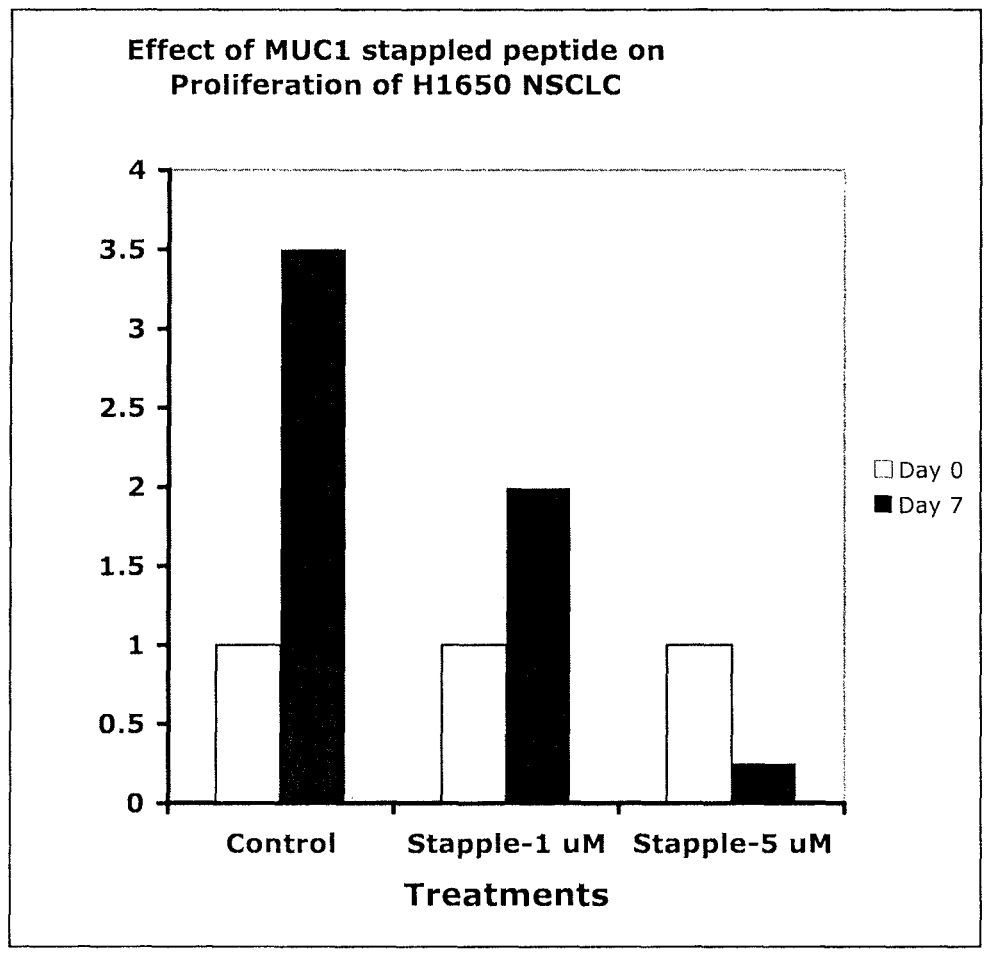
FIG. 9A. Effects of MUC1-CD-stapled peptide on the growth of H1650 non-small cell lung carcinoma cells. To assess sensitivity to inhibition of MUC1 function, H1650 non-small cell lung carcinoma (NSCLC) cells were treated with 1 and 5 µM MUC1 CQC stapled peptide (GO-200-1B) for 7 days. Treatment of H1650 cells with 5 µM GO-200-1B was associated with significant inhibition of growth and then a decrease in cell number. Y-axis represents—fold growth as compared to control untreated cells on day 0.
Figure 9B:
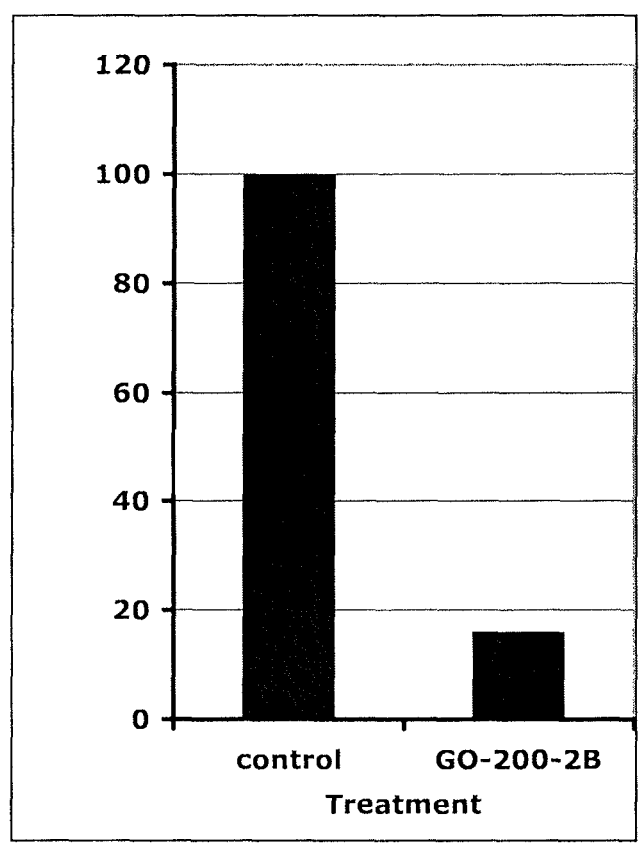
FIG. 9B. Effect of GO-200-2B on cell proliferation. H-1975 non-small cell lung carcinoma cell line was gown in DMEM with 10% heat-inactivated fetal bovine serum with 100 units/mL penicillin, 100 µg/ml streptomycin and 2 mmol/L L-glutamine. Cells were re-seeded one day before treatments. Cells were treated with 5 µM GO-200-2B for 3 days and cell viability was determined by trypan blue exclusion. Y-axis represents percent viability as compared to control untreated cells.
Figure 10:
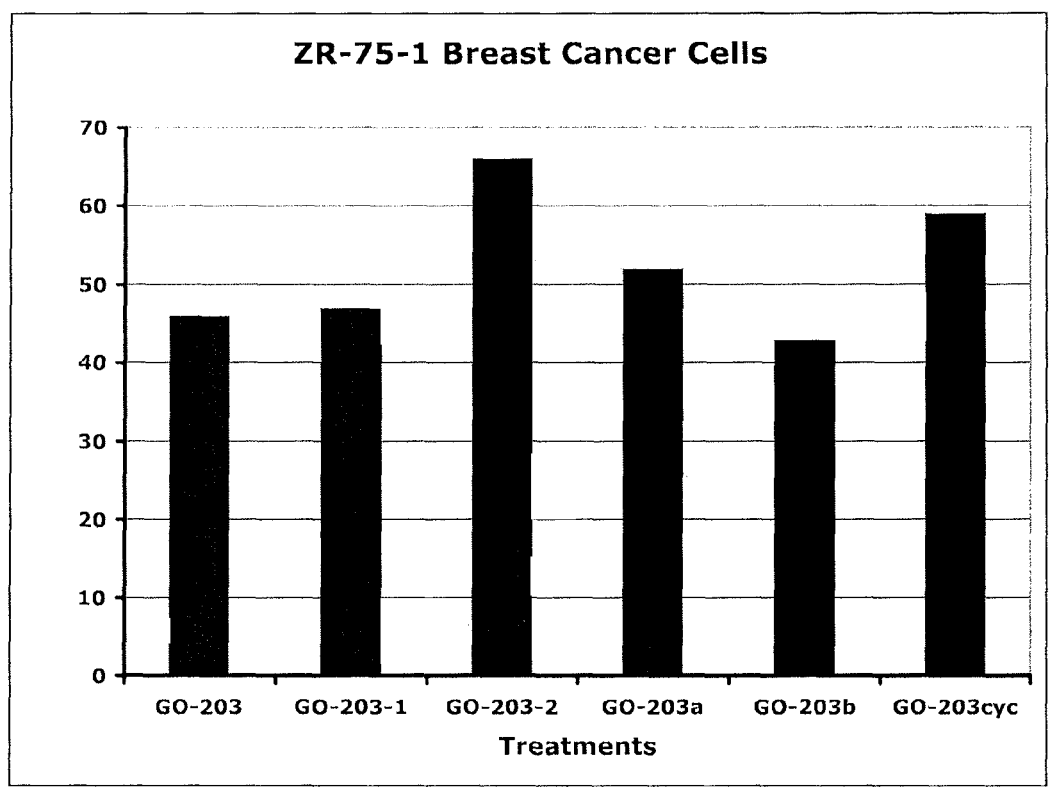
FIG. 10. Effect of different MUC1-CD CQC-region peptides on the growth of hormone-dependent breast carcinoma cells. To determine whether exposure to different MUC1-CD CQC-region containing peptides affect growth, ZR-75-1 breast carcinoma cells were treated with 5 µM of different peptides for 4 days and monitored for cell proliferation. Significantly, there was a substantial growth inhibition compared with that in cells left untreated. Y-axis represents percent growth inhibition as compared to control untreated cells.
Figure 11:
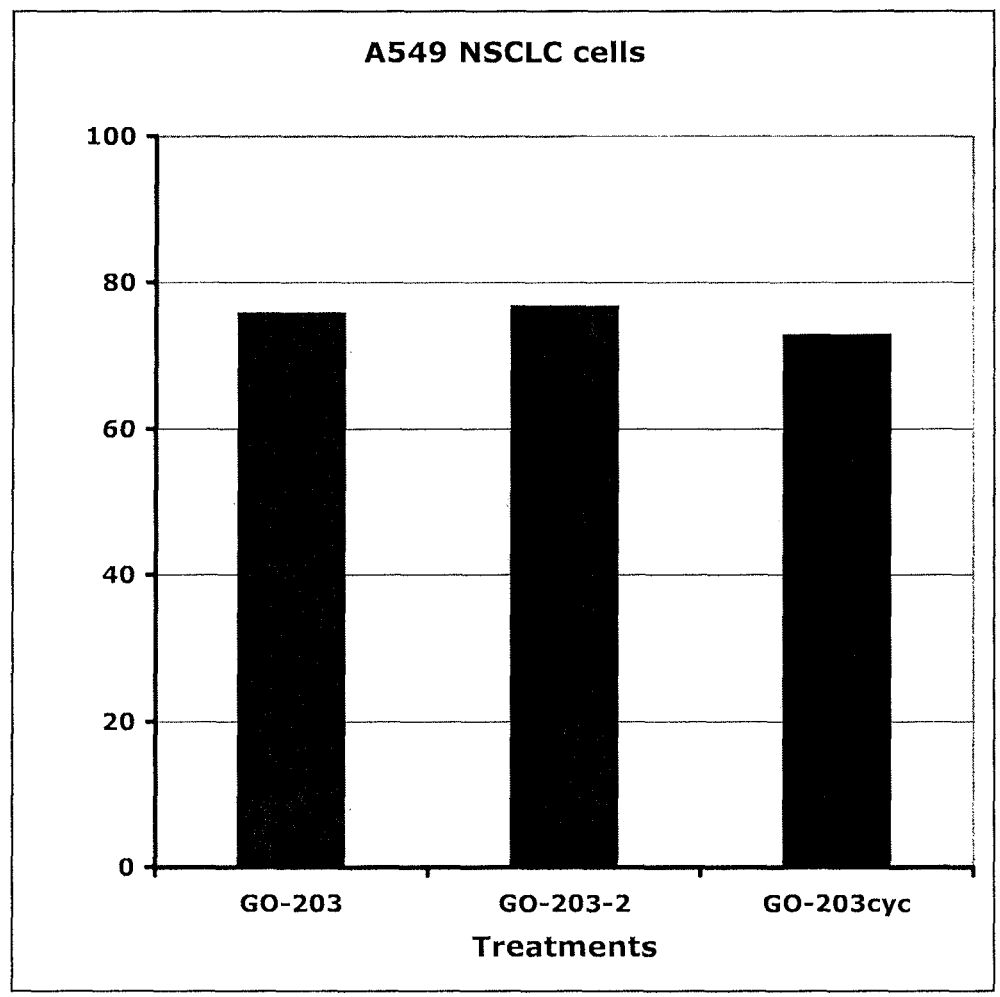
FIG. 11. Effect of different MUC1-CD CQC-region peptides on the growth of non small cell carcinoma cells. A549 non-small cell lung carcinoma cells were treated with 5 µM GO-203, GO-203-2 or GO-203cyc for 7 days. Viable cell number on day 7 was determined by trypan blue exclusion and percent growth inhibition was calculated by comparing the cell growth of untreated cells. Y-axis represents percent growth inhibition as compared to control untreated cells.
Figure 12:
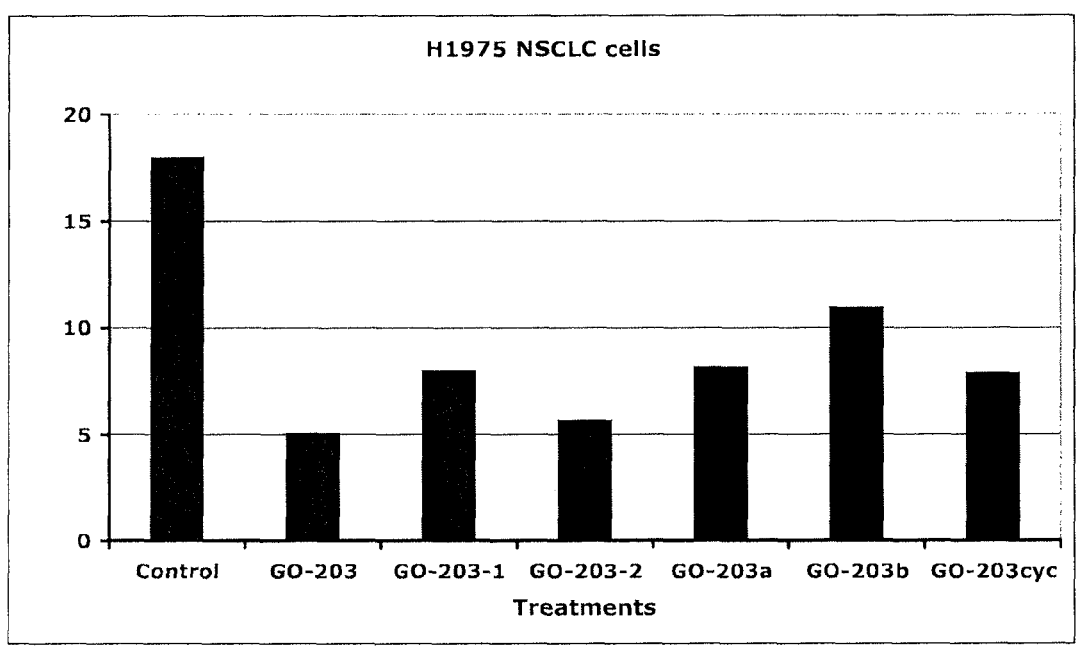
FIG. 12. Effect of different MUC1-CD CQC-region peptides on the growth of H1975 non small cell carcinoma cells. H1975 non-small cell lung carcinoma cells were treated with 5 µM of different MUC1-CD CQC-region peptides for 6 days. Viable cell number on day 6 was determined by trypan blue exclusion. The results demonstrate that treatment of H1975 cells with 5 µM of different peptides was associated with significant inhibition of growth. Y-axis represents relative growth as compared to control untreated cells.
Figure 14:
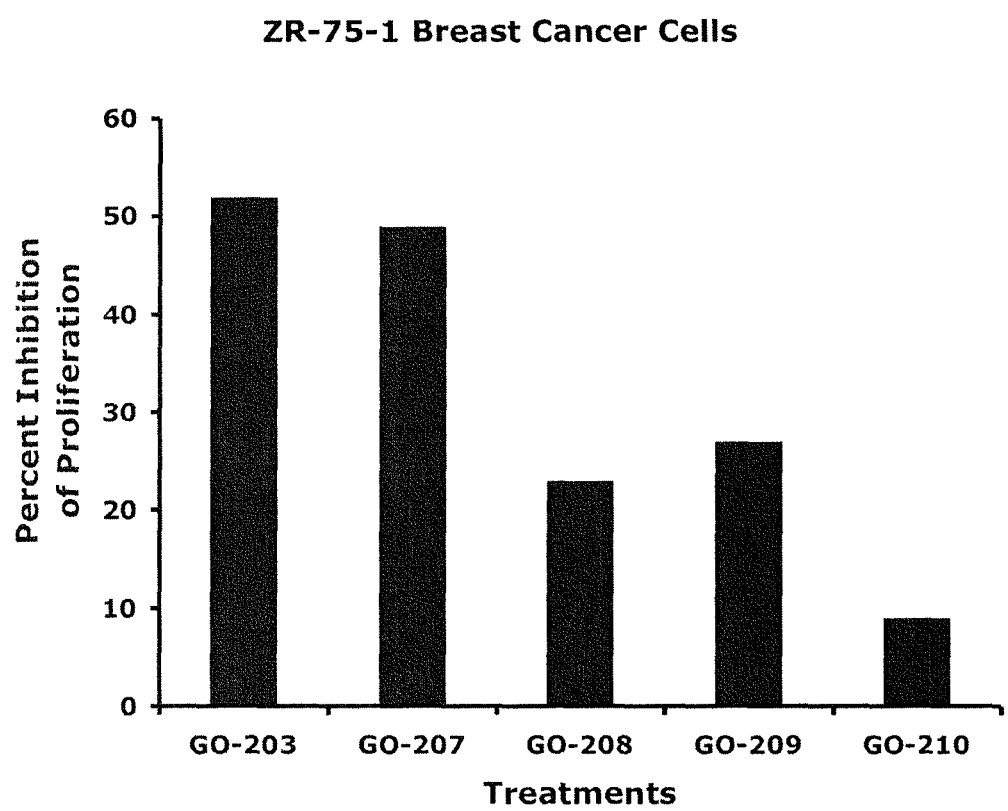
FIG. 14. Effect of Shorter GO-203 peptides on proliferation of ZR-75-1 Breast Cancer Cells. Human ZR-75-1 breast cancer cells were grown in RPMI1640 supplemented with 10% heat-inactivated fetal bovine serum, 100 units/ml penicillin, 100 µg/ml streptomycin. Cells were treated with different peptides at 5 µM every day for four days and cell viability was determined by trypan blue exclusion. In contrast to GO-210, treatment of ZR-75-1 breast carcinoma cells with 5 µM GO-203 (SEQ ID NO:53), GO-207 (SEQ ID NO:4), GO-208 (SEQ ID NO:50) and GO-209 (SEQ ID NO:54) every day for 4 days was associated with significant inhibition of growth.
Figure 15:
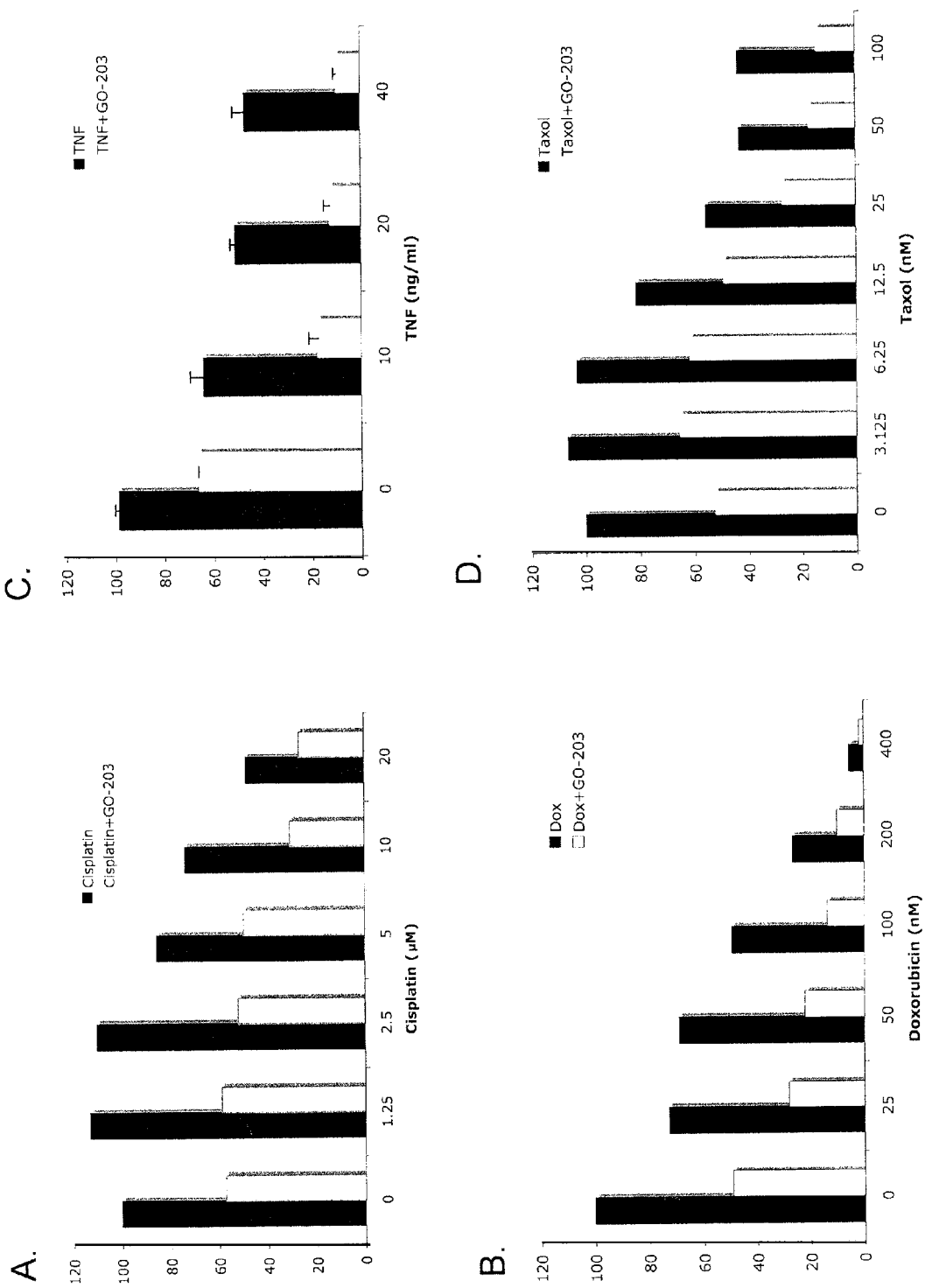
FIGS. 15A-D. Effects of GO-203 in combination with different anti-cancer drugs. ZR-75-1 cells were exposed to the indicated concentrations of Cisplatin (FIG. 15A), Doxorubicin (FIG. 15B), rh-TNF-α (FIG. 15C) and Taxol (FIG. 15D) alone and in combination with GO-203. The treatment was sequential for Cisplatin, Doxorubicin and Taxol where cells were exposed to these agents for 72 h followed by treatment with 5 µM of GO-203 for 72 h. In studies with rh-TNF, cells were exposed concomitantly to different concentrations of rh-TNF alone and in combination with 5 µM of GO-203 for 72 h. The MTS assay was used to determine the cell survival. For all panels, the Y-axis represents percent growth as compared to control untreated cells.
Figure 16:
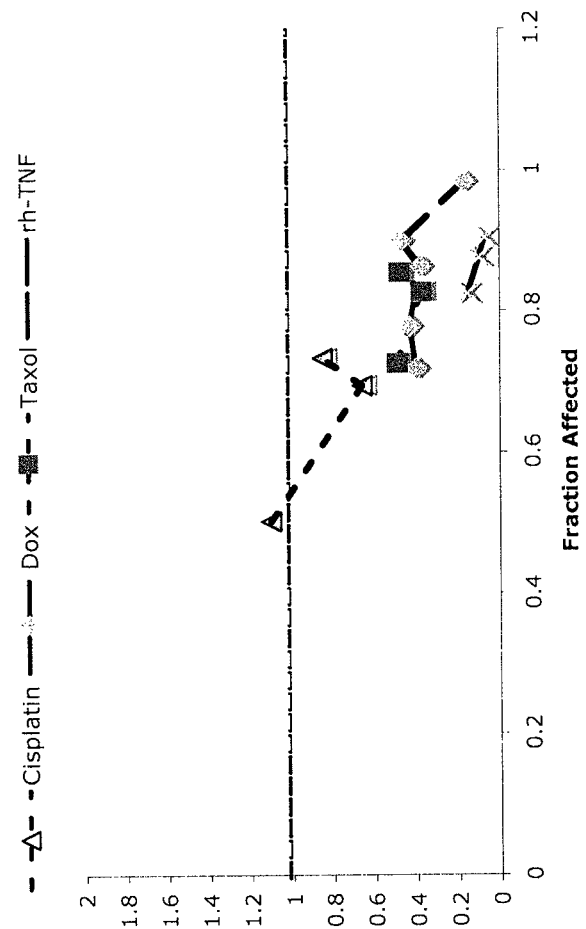
FIG. 16. GO-203 is additive or synergistic with anti-cancer agents. The plots show combination indexes against different effect levels (fraction affected). The effect level was obtained by treating cells with the indicated combinations of anti-cancer drugs and GO-203. Y-axis represents—fold growth as compared to control untreated cells.

To determine whether exposure to GO-200-1B affects growth of non-small cell lung carcinoma cells, H-1650 cells were treated with 1 and 5 μM GO-200-1B for 7 days and monitored for growth. The results demonstrate that treatment of cells with 5 μM GO-200-1B was associated with significant inhibition of growth (FIG. 9A). Moreover, another non-small cell lung carcinoma cell line, H-1975, was treated with 5 μM GO-200-2B for 3 days and monitored for cell growth as well as cell death. The results demonstrate that treatment of H-1975 cells with GO-200-2B for 3 days was associated with more than 80% inhibition of cell proliferation. Moreover, GO-200-2B was also associated with significant induction of cell death (FIG. 9B). These findings indicate that stapled MUC1-C peptides are effective in inducing growth arrest and death of human MUC1-positive cancer cells.

GO-203 analogs. The inventors' recent studies have shown that a MUC1 C-terminal peptide (CQCRRKNYGQLDIFP) is active in inhibiting growth of multiple carcinoma cell lines. They have also demonstrated that a shorter MUC1-C-terminal peptide, CQCRRKN, is also active in killing tumor cells. However, these MUC1-C-terminal peptides consists of L-amino acids. Importantly, peptides with L-amino acids have susceptible to degradation by proteolytic enzymes, whereas those containing D-amino acids have been shown to be more stable. Consequently, they have generated an all-dextro form of the above described shorter MUC1 C-terminal peptide, in which the L-amino acids were changed to D-amino acids (GO-203). Moreover, to determine the minimum amino acid residues from the MUC1-C-terminal region that are required to retain the cell killing activity, they have also generated many different versions of GO-203 as described in FIG. 8.

Multiple tumor cell lines (ZR-75-1 Hormone-dependent Breast Carcinoma; MDA-MB-231 Triple-Negative Breast Carcinoma; A549 Non-small Cell Lung Carcinoma; H-1975 Non-small Cell Lung Carcinoma) were grown in RPMI-1640 supplemented with 10% heat-inactivated fetal bovine serum, 100 units/mL penicillin and 100 μg/mL streptomycin and 2 mmol/L L-glutamine. Cells were treated separately with 5 μM of different analogs of GO-203 (FIG. 8) for 3 to 7 days and viability was determined by trypan blue exclusion. The proliferation of different cell lines was compared with cells treated with vehicle only. The results demonstrate that treatment of multiple tumor cell lines with 5 μM of different analogs of GO-203 was associated with significant inhibition of growth (FIGS. 10-14).

Combination therapy. The combination index (CI) values generated by the CombiTool program were plotted against the fraction affected by the drug combination. The CI values were close to 1 for Cisplatin and GO-203, indicating an additive interaction. The CI values obtained for Doxorubicin (25, 50, 100, 200 nM), Taxol (25, 50, 100 nM) and TNF (10, 20, 40 ng/ml) with GO-203 were less than 1, supporting a strong additive effect or synergism (FIGS. 15A-D and 16).

Example 3

Discussion

MUC1/CQC peptide blocks MUC1 oligomerization. Overexpression of MUC1 is sufficient for the induction of anchorage-independent growth and tumorigenicity (Li et al., 2003a; Huang et al., 2003; Huang et al., 2005). Notably, however, the MUC1 transforming function is abrogated by mutation of the CQC motif in the cytoplasmic domain to AQA (Leng et al., 2007). MUC1 forms oligomers and the CQC motif is necessary for this oligomerization (Leng et al., 2007). Moreover, oligomer formation is necessary for targeting of the MUC1-C subunit to the nucleus (Leng et al., 2007). Other functions of the MUC1-C subunit, such as activation of the Wnt/β-catenin and IKKβ→NF-κB pathways, are also dependent on the formation of MUC1-C oligomers (unpublished data). Based on these findings, the inventors reasoned that disruption of MUC1 oligomerization by a small molecule would have the potential to block the MUC1 transforming function. In that context, they synthesized a MUC1-derived peptide that contains the CQC motif and a poly-Arg cell delivery domain for entry into cells. Initial studies with this MUC1/CQC peptide showed that it inhibits oligomerization of MUC1-CD in vitro. As shown previously by BIAcore analysis, MUC1-CD forms dimers with a dissociation constant (Kd) of 33 nM (Leng et al., 2007). The MUC1/CQC peptide similarly bound to MUC1-CD with a Kd of 30 nM. In addition, the demonstration that the MUC1/AQA peptide has little if any effect on MUC1 oligomerization provided support for dependence on the CQC motif. MUC1/CQC, and not MUC1/AQA, was also effective in blocking MUC1-CD oligomerization in cells. These findings thus indicated that the MUC1/CQC peptide could be used to disrupt MUC1 oligomerization and potentially thereby MUC1 function in human breast carcinoma cells.

Selectivity of the MUC1/CQC peptide for MUC1 overexpressing carcinoma cells. Cell delivery domains, such as poly-D-Arg, and their conjugates enter cells, at least in large part, by endocytosis and then need to reach their intended target (Fischer, 2007). Entry of the MUC1/CQC peptide into ZR-75-1 breast cancer cells was readily detectable and persisted for at least 24 h. Significantly and consistent with nuclear targeting of MUC1 being dependent on oligomerization (Leng et al., 2007), uptake of the MUC1/CQC peptide was associated with down-regulation of MUC1-C levels in the nucleus. Similar results were obtained with MCF-7 breast cancer cells, indicating that this response to the MUC1/CQC peptide is not cell specific. Moreover and notably, exposure of these cells to MUC1/CQC, and not MUC1/AQA, was associated with growth arrest and the induction of necrosis. Of importance is whether MUC1/CQC induces death by a mechanism dependent on expression of its intended target or is a non-specific cytotoxin. In that context, silencing MUC1 in ZR-75-1 cells abrogated the MUC1/CQC cytotoxic effects. By contrast, exposure of non-malignant MCF-10A mammary epithelial cells to the MUC1/CQC peptide had little effect. These findings indicate that sensitivity to the MUC1/CQC peptide is dependent on overexpression of MUC1 and a function of MUC1 associated with the malignant phenotype. The MUC1/CQC peptide thus appears to have a dominant-negative activity that is selective for carcinoma cells overexpressing MUC1.

Anti-tumor activity of the MUC1/CQC peptide. Cell delivery domains are being used to deliver therapeutic cargoes (Fischer, 2007). However, as with any of these agents, an overriding issue is whether the MUC1/CQC peptide can be delivered in vivo with an effective therapeutic index, that is anti-tumor activity and an acceptable toxicity profile. In addressing this issue, the inventors found that administration of the MUC1/CQC peptide at 10 and 30 mg/kg/d for 21 d was well-tolerated without apparent acute toxicities. They also found that treatment at these doses was effective in abrogating tumor growth. These results were in contrast to administration of the MUC1/AQA peptide at 50 mg/kg/d for 21 d, which had no anti-tumor activity. Moreover and somewhat surprisingly, there was no evidence for tumor regrowth after dosing at 30 mg/kg/d for 21 d. Administration of the MUC1/CQC peptide at 50 mg/kg/d for 7 d also demonstrated that tumor growth remains arrested for extended periods following treatment. These results are explained, at least in part, by the finding that treatment with the MUC1/CQC peptide is associated with the induction of tumor necrosis.

The in vitro activity of the MUC1/CQC 7-mer is as potent as the MUC1/CQC 15-mer. Based on these findings, one would anticipate that the MUC1/CQC 7-mer will also be active as an anti-tumor agent in in vivo tumor models.

\*\*\*\*\*\*\*\*\*\*\*\*\*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976

U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Patent Appln. 2005/0015232
Abe and Kufe, *Cancer Res.*, 49(11):2834-2839, 1989.
Ahmad et al., *Nat. Cell Biol.*, 9:1419-1427, 2007.
Baldus et al., *Clin. Cancer Res.*, 10(8):2790-2796, 2004.
Bodanszky et al., *J. Antibiot.*, 29(5):549-53, 1976.
Cohen et al., *J. Med. Chem.*, 33:883-894, 1990.
Culver et al., *Science*, 256(5063):1550-1552, 1992.
Duraisamy et al., *Gene*, 373:28-34, 2006.
Fischer, *Med. Res. Rev.*, 27(6):755-796, 2007.
Gendler et al., *J. Biol. Chem.*, 263:12820-12823, 1988.
Gronenborn et al., *Anal. Chem.*, 62(1):2-15, 1990.
Hodel et al., *Mol. Cell*, 10(2):347-58, 2002.
Huang et al., *Cancer Biol Ther.*, 2:702-706, 2003.
Huang et al., *Cancer Res.*, 65:10413-10422, 2005.
Jackson, *Seminars in Oncology*, 24:L164-172, 1997.
Johnson et al., In: *Biotechnology And Pharmacy*, Pezzuto et al. (Eds.), Chapman and Hall, NY, 1993.
Jones et al., *J. Med. Chem.*, 39:904-917, 1996.
Kau et al., *Nat. Rev. Cancer*, 4(2):106-17, 2004.
Kinlough et al., *J. Biol. Chem.*, 279(51):53071-53077, 2004.
Kufe et al., *Hybridoma*, 3:223-232, 1984.
Kufe, *Cancer Biol. Therapy*, 7:81-84, 2008.
Leng et al., *J. Biol. Chem.*, 282:19321-19330, 2007.
Levitan et al., *J. Biol. Chem.*, 280:33374-33386, 2005.
Li et al., *Cancer Biol. Ther.*, 2:187-193, 2003b.
Li et al., *J. Biol. Chem.*, 276:35239-35242, 2001.
Li et al., *J. Biol. Chem.*, 276:6061-6064, 2001.
Li et al., *Mol. Cancer Res.*, 1:765-775, 2003c.
Li et al., *Mol. Cell Biol.*, 18:7216-7224, 1998.
Li et al., *Oncogene*, 22:6107-6110, 2003a.
Ligtenberg et al., *J. Biol. Chem.*, 267, 6171-6177, 1992.
Macao, *Nat. Struct. Mol. Biol.*, 13, 71-76, 2006.
McPherson, *J. Biol. Chem.*, 251:6300-6306, 1976.
Merlo et al., *Cancer Res.*, 49, 6966-6971, 1989.
Merrifield, *J. Am. Chem. Soc.*, 85:2149-2154, 1963.
Muthuswamy, *Nat. Cell Biol.*, 3(9):785-92, 2001.
Navia et al., *Curr. Opin. Struct. Biol.*, 2:202-210, 1992.
PCT Appln. PCT/US00/03745
PCT Appln. PCT/US00/14667
PCT Appln. PCT/US99/11913
PCT Appln. PCT/US99/18441
Peptide Synthesis, 1985
Percipalle et al., *J. Mol. Biol.*, (4):722-32, 1997.
Perey et al., *Cancer Res.*, 52(22):6365-6370, 1992.
Protective Groups in Organic Chemistry, 1973
Protein NMR Spectroscopy, Principles and Practice, J. Cavanagh et al., Academic Press. San Diego, 1996.
Raina et al., *EMBO J.*, 25:3774-3783, 2006.
Raina et al., *J. Biol. Chem.*, 279:20607-20612, 2004.
Ramasamy et al., *Mol. Cell*, 27:992-1004, 2007.
Remington's Pharmaceutical Sciences, 15th Ed., 1035-1038 and 1570-1580, 1990.
Remington's Pharmaceutical Sciences, 15th Ed., 3:624-652, 1990.
Ren et al., *Cancer Cell*, 5:163-175, 2004.
Ren et al., *J. Biol. Chem.*, 277:17616-17622, 2002.
Ren et al., *Oncogene*, 25:20-31, 2006.
Ryan and Wente, *Curr. Opin. Cell Biol.*, 12(3):361-71, 2000.
Schroeder et al., *J. Biol. Chem.*, 276(16):13057-13064 2001.
Schroeder et al., *Oncogene*, 23:5739-5747, 2004.
Siddiqui et al., *Proc. Natl. Acad. Sci. USA*, 85:2320-2323, 1988.
Solid Phase Peptide Synthelia, 1984
Soule et al., *Cancer Res.*, 50(18):6075-6086, 1990.
Suh and Gumbiner, *Exp. Cell Res.*, 290(2):447-56, 2003.
Truscott et al., *J. Cell Biol.*, 163(4):707-713, 2003.
Vermeer et al., *Nature*, 422(6929):322-6, 2003.
Weber, *Advances Protein Chem.*, 41:1-36, 1991.
Wei et al., *Cancer Cell*, 7:167-178, 2005.
Weis, *Cell*, 112(4):441-51, 2003.
Wen et al., *J. Biol. Chem.*, 278:38029-38039, 2003.
Wider, *BioTechniques*, 29:1278-1294, 2000.
Yamamoto et al., *J. Biol. Chem.*, 272:12492-12494, 1997.
Yin et al., *J. Biol. Chem.*, 278:35458-35464, 2003b.
Yin et al., *J. Biol. Chem.*, 279:45721-45727, 2004.
Yin et al., *J. Biol. Chem.*, 282:257-266, 2007.
Young et al., *Cell.* 112(1):41-50, 2003.

What is claimed is:

1. A method of inhibiting a human Mucin 1 (MUC1)-positive tumor cell in a human subject comprising administering to said subject a MUC1 peptide of at least 6 consecutive human MUC1 residues and no more than 20 consecutive human MUC1 residues and comprising the sequence CQCRRK (SEQ ID NO: 4), wherein the amino-terminal cysteine of CQCRRK is covered on its NH$_2$-terminus by at least one amino acid residue that need not correspond to the native MUC-1 transmembrane sequence.

2. The method of claim 1, wherein said peptide comprises at least 5, 6, 7 or 8 consecutive MUC1 residues.

3. The method of claim 1, wherein said peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

4. The method of claim 1, wherein the MUC1-positive tumor cell is a carcinoma cell, a leukemia cell or a myeloma cell.

5. The method of claim 4, wherein the carcinoma cell is a prostate or breast carcinoma cell.

6. The method of claim 1, wherein said peptide is fused to a cell delivery domain.

7. The method of claim 6, wherein said cell delivery domain is poly-D-R, poly-D-P or poly-D-K.

8. The method of claim 1, wherein administering comprises intravenous, intra-arterial, intra-tumoral, subcutaneous, topical or intraperitoneal administration.

9. The method of claim 1, wherein administering comprises local, regional, systemic, or continual administration.

10. The method of claim 1, wherein inhibiting comprises inducing growth arrest of said tumor cell, apoptosis of said tumor cell and/or necrosis of a tumor tissue comprising said tumor cell.

11. The method of claim 1, further comprising administering to said subject a second anti-cancer therapy.

12. The method of claim 11, wherein said second anti-cancer therapy is surgery, chemotherapy, radiotherapy, hormonal therapy, toxin therapy, immunotherapy, and cryotherapy.

13. The method of claim 11, wherein said second anticancer therapy is administered prior to said peptide.

14. The method of claim 11, wherein said second anticancer therapy is administered after said peptide.

15. The method of claim 11, wherein said second anticancer therapy is administered at the same time as said peptide.

16. The method of claim 1, wherein said peptide is administered at 0.1-500 mg/kg/d.

17. The method of claim 1, wherein said peptide is administered at 10-100 mg/kg/d.

18. The method of claim 1, wherein said peptide is administered daily.

19. The method of claim 18, wherein said peptide is administered daily for 7 days, 2 weeks, 3 weeks, 4 weeks, one month, 6 weeks, 8 weeks, two months, 12 weeks, or 3 months.

20. The method of claim 1, wherein said peptide is administered weekly.

21. The method of claim 20, wherein said peptide is administered weekly for 2 weeks, 3 weeks, 4 weeks, 6 weeks, 8 weeks, 10 weeks, or 12 weeks.

22. The method of claim 1, wherein said peptide comprises all L amino acids.

23. The method of claim 1, wherein said peptide comprises all D amino acids.

24. The method of claim 1, wherein said peptide comprises a mix of L and D amino acids.

25. The method of claim 1, further comprising the step of assessing the expression of MUC1 in a tumor cell of said subject prior to administering said peptide.

26. The method of claim 1, further comprising the step of assessing the effect of said peptide on the expression of MUC1 in a tumor cell of said subject.

* * * * *

UNITED STATES PATENT AND TRADEMARK OFFICE
CERTIFICATE OF CORRECTION

PATENT NO. : 8,524,669 B2
APPLICATION NO. : 12/580865
DATED : September 3, 2013
INVENTOR(S) : Donald W. Kufe and Surender Kharbanda It is certified that error appears in the above-identified patent and that said Letters Patent is hereby corrected as shown below:

In title page, item (56) References Cited - Other Publications, delete the 6th reference on page 1 "Spicer et al, Molecular Cloning and Analysis of the Mouse Homologue of the Tumor-associated Mucin, MUC1R, eveals Conservation of Potential O-Glycosylation Sites, Transmembrane, and Cytoplasmic Domains and a Loss of Minisatellite-like Polymorphism, The Journal of Biological Chemistry, 1991, 266, pp. 15099-15109." and replace with --Spicer et al, Molecular Cloning and Analysis of the Mouse Homologue of the Tumor-associated Mucin, MUC1R, Reveals Conservation of Potential O-Glycosylation Sites, Transmembrane, and Cytoplasmic Domains and a Loss of Minisatellite-like Polymorphism, The Journal of Biological Chemistry, 1991, 266, pp. 15099-15109.-- therefor.

In title page, item (56) References Cited - Other Publications, delete the 14th reference on page 1 "Kinlough et al., "Recycling of MUC1 is dependent on its palmitoylation," The Journal of Biological Chemistry, 281(17):121 12-12122, 2006." and replace with --Kinlough et al., "Recycling of MUC1 is dependent on its palmitoylation," The Journal of Biological Chemistry, 281(17):12112-12122, 2006.-- therefor.

In title page, item (56) References Cited - Other Publications, delete the 5th reference on page 2 "PCT International Search Report and Written Opinion, issued in International application No. PCT?US2009/061051, dated Nov. 26, 2010." and replace with --International Search Report and Written Opinion, issued in International application No. PCT/US2009/061051, dated Nov. 26, 2010.-- therefor.

In title page, item (56) References Cited - Other Publications, delete the 18th reference on page 1 "Yin et al., "MUC1-C oncoprotein suppresses reactive oxygen species-induced terminal differentiation of acute myelogenous leukemia cells," Blood., 1 17(18):4863-4870, May 5, 2011. E-published Mar. 21, 2011. D01:10.1182/blood-2010-296632." and replace with --Yin et al., "MUC1-C oncoprotein suppresses reactive oxygen species-induced terminal differentiation of acute myelogenous leukemia cells," Blood., 117 (18):4863-4870, May 5, 2011. E-published Mar. 21, 2011. D01:10.1182/blood-2010-296632.-- therefor.

Signed and Sealed this
Third Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,524,669 B2 | Page 1 of 1 |
| APPLICATION NO. | : 12/580865 | |
| DATED | : September 3, 2013 | |
| INVENTOR(S) | : Donald W. Kufe et al. | |

It is certified that error appears in the above-identified patent and that said Letters Patent is hereby corrected as shown below:

In column 1, beginning on line 9, insert --This invention was made with government support under grant number CA097098 awarded by The National Institutes of Health. The government has certain rights in the invention.--

Signed and Sealed this
Fifteenth Day of November, 2016

Michelle K. Lee
*Director of the United States Patent and Trademark Office*